United States Patent
Zagar et al.

(10) Patent No.: US 6,888,003 B2
(45) Date of Patent: May 3, 2005

(54) METHOD FOR PRODUCING 7-(PYRAZOLE-3-YL) BENZOXAZOLES

(75) Inventors: Cyrill Zagar, Ludwigshafen (DE); Robert Reinhard, Ludwigshafen (DE); Michael Puhl, Lampertheim (DE); Thorsten Volk, Mannheim (DE); Norbert Götz, Worms (DE); Gerhard Hamprecht, Weinheim (DE); Olaf Menke, Altleiningen (DE); Ingo Sagasser, Dannstadt-Schauernheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 143 days.

(21) Appl. No.: 10/221,206

(22) PCT Filed: Mar. 15, 2001

(86) PCT No.: PCT/EP01/02947

§ 371 (c)(1),
(2), (4) Date: Sep. 10, 2002

(87) PCT Pub. No.: WO01/68644

PCT Pub. Date: Sep. 20, 2001

(65) Prior Publication Data

US 2003/0050477 A1 Mar. 13, 2003

(30) Foreign Application Priority Data

Mar. 16, 2000 (DE) .......................... 100 12 804

(51) Int. Cl.[7] .......................... C07D 498/00
(52) U.S. Cl. .......................... 548/218
(58) Field of Search ................ 548/218, 364, 548/4, 376.1, 1

(56) References Cited

U.S. PATENT DOCUMENTS

| | | | |
|---|---|---|---|
| 5,401,700 A | 3/1995 | Sohn et al. | 504/106 |
| 5,945,382 A | 8/1999 | Cantegril et al. | 504/280 |
| 5,945,541 A | 8/1999 | Sohn et al. | 548/374 |
| 6,232,470 B1 | 5/2001 | Zagar et al. | 548/217 |
| 6,482,774 B1 | 11/2002 | Zagar et al. | 504/267 |

FOREIGN PATENT DOCUMENTS

| | | |
|---|---|---|
| WO | 95/19358 | 7/1995 |
| WO | WO 96/02138 | 2/1996 |
| WO | WO 98/27090 | 6/1998 |
| WO | WO 99/55702 | 11/1999 |

OTHER PUBLICATIONS

Kraus et al. "Quinone Diazide Cyclizations—A Direct Route to Dihydropenzofurans" Tetrahedron vol. 41 No. 12, (1985) pp. 2337–2340.

Bowman et al. "Intramolecular Aromatic Substitution ($S_{RN}1$) Reactions: Use of Entrainment for the Preparation of Rencoghiazoles" Tetrahedron Letters vol. 23 No. 48 (1982) pp. 5093–5096.

Minami et al. "Copper(1) Salt-Mediated Arylation of Phosphinyl-Stabilized Carbanions and Synthetic Apllication to Heterocyclic Compounds" J. Org. Chem. vol. 58, (1993) pp. 7009–7015.

R. J. Perry J. Org. Chem. vol. 57 No. 23, (1992) pp. 6351–6354.

*Primary Examiner*—Joseph K. McKane
*Assistant Examiner*—Robert Shiao
(74) *Attorney, Agent, or Firm*—Keil & Weinkauf

(57) ABSTRACT

A process for preparing 7-(pyrazol-3-yl)benzoxazoles of the formula I

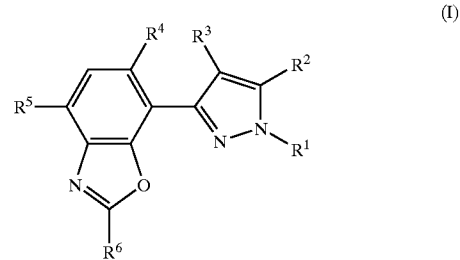

(I)

in which the variables $R^1$–$R^6$ are as defined in claim 1, which process is characterized in that a 2-halo-3-(pyrazol-3-yl)anilide of the formula II,

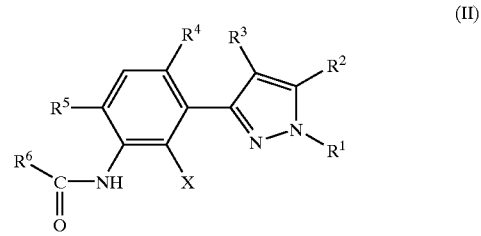

(II)

in which X is bromine or iodine is reacted with a base in the presence of a transition metal compound of subgroup VIIa, VIIIa or Ib of the Periodic Table of the Elements, is disclosed.

9 Claims, No Drawings

METHOD FOR PRODUCING 7-(PYRAZOLE-3-YL) BENZOXAZOLES

This application is a 371 of PCT/EP01/02347 filed on Mar. 15, 2001.

The invention relates to a process for preparing 7-(pyrazol-3-yl)benzoxazoles of the formula I

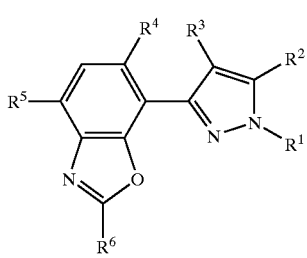

in which the variables $R^1$–$R^6$ are as defined below:

$R^1$ is hydrogen, $C_1$–$C_4$-alkyl or $C_1$–$C_4$-haloalkyl;

$R^2$ is cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl;

$R^3$ is hydrogen, halogen, cyano, $C_1$–$C_4$-alkyl or $C_1$–$C_4$-haloalkyl;

$R^4$ is halogen;

$R^5$ is fluorine, chlorine or cyano;

$R^6$ is hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_1$–$C_4$-alkoxy-$C_1$–$C_4$-alkyl, $C_1$–$C_4$-cyanoalkyl, $C_1$–$C_4$-alkylthio-$C_1$–$C_4$-alkyl, ($C_1$–$C_4$-alkoxy)carbonyl-$C_1$–$C_4$-alkyl, $C_3$–$C_8$-cycloalkyl, $C_3$–$C_8$-cycloalkyl-$C_1$–$C_4$-alkyl, $C_3$–$C_8$-cycloalkyloxy-$C_1$–$C_4$-alkyl, phenyl, phenyl-$C_1$–$C_4$-alkyl, 4- to 7-membered heterocyclyl or heterocyclyl-$C_1$–$C_4$-alkyl, where each cycloalkyl, phenyl and heterocyclyl ring can be unsubstituted or may carry one, two or three substituents selected independently of one another from the group consisting of cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio.

7-(Pyrazol-3-yl)benzoxazoles of the formula I are disclosed in WO 98/27090 and WO 99/55702. These compounds are highly effective herbicides.

In the prior art, their preparation is described starting from 3-(pyrazol-3-yl)anilines of the formula III

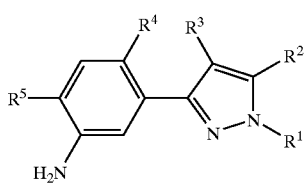

where initially the amino group in the aniline III is converted, via a diazonium intermediate, into an azide group. This azide is then reacted with a carboxylic acid $R^6$—COOH to give the benzoxazole of the formula I. Here, it is possible, on the one hand, to react the azide directly with the carboxylic acid to give the benzoxazole. Alternatively, the azide can be reacted with an organic sulfonic acid to give, via a sulfuric acid ester intermediate, the corresponding 2-hydroxy-3-pyrazolylaniline, which is then cyclized with a carboxylic acid $R^6$—COOH or a derivative thereof to give the benzoxazole.

These preparation processes are highly problematic, since azides can decompose explosively (see, for example, Houben-Weyl, Methoden der organischen Chemie [Methods of Organic Chemistry], Vol. 10/3, Georg-Thieme Verlag Stuttgart, 1965, p.782). Moreover, in the present case, the conversion of the azide into the target compound I proceeds with insufficient yields and with the formation of numerous byproducts. The removal of the byproducts is complicated and in some cases problematic or not possible.

G. A. Kraus et al., Tetrahedron 41 (1985), 2337–2340, describe the preparation of 3,5-dibromoorthoquinone diazide from a benzoxazole derivative. The benzoxazole derivative is prepared by reaction of 2,4,6-triibromoacetanilide in the presence of sodium hydride and an excess of copper bromide, in hexamethylphosphoric triamide.

W. R. Bowman et al., Tetrahedron Letters 23 (1982), 5093–5096, describe, in the course of their studies on the conversion of thiocarboxanilides into benzothiazoles, also the conversion of ortho-iodobenzanilide into 2-phenyl-1,3-benzoxazole in the presence of copper iodide.

During the reaction of N-(2-iodophenyl)-N-methyl-α-diethoxyphosphinyl)acetamide in the presence of equimolar amounts of sodium hydride and a two-fold molar excess of copper iodide, T. Minami et al., J. Org. Chem. 58 (1993), 7009–7015, observed the formation of 2-[(diethoxyphosphinyl)methyl]benzoxazole.

None of the abovementioned processes describes the preparation of heterocyclically substituted benzoxazoles. The number of substituents at the phenyl ring of benzoxazole is limited to 2.

It is an object of the present invention to provide a process for preparing 7-(pyrazol-3-yl)benzoxazoles of the formula I in which an azide intermediate is avoided.

We have found that this object is achieved by a process in which a 2-halo-3-(pyrazol-3-yl)anilide of the formula II

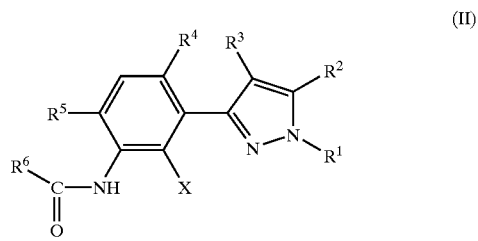

in which the variables $R_1$–$R^6$ are as defined above and X is bromine or iodine, is reacted with a base in the presence of a transition metal compound of subgroups VIIa, VIIIa or Ib of the Periodic Table of the Elements.

Accordingly, the present invention relates to a process for preparing 7-(pyrazol-3-yl)benzoxazoles of the formula I as defined above, which comprises reacting a 2-halo-3-(pyrazol-3-yl)anilide of the formula II as defined above with a base in the presence of a transition metal compound of subgroup VIIa, VIIIa or Ib of the Periodic Table of the Elements, to give a compound of the formula I.

The organic molecule moieties mentioned in the definition of the substituents $R^1$, $R^2$, $R^3$, $R^4$, $R^5$ and $R^6$ or as radicals on cycloalkyl, phenyl or heterocyclic rings are collective terms for individual enumerations of the individual group members. All hydrocarbon chains, i.e. all alkyl, haloalkyl, phenylalkyl, cycloalkylalkyl, alkoxy, haloalkoxy, alkylthio, haloalkylthio, alkylsulfinyl, haloalkylsulfinyl, alkylsulfonyl, haloalkylsulfonyl, alkenyl, haloalkenyl and alkynyl groups and corresponding moieties in larger groups, such as alkoxycarbonyl, phenylalkyl-, cycloalkylalkyl, alkoxycarbonylalkyl, etc., can in each case be straight-chain or branched, where the prefix $C_n$–$C_m$ in each case indicates the possible number of carbon atoms in the group. Halogenated substituents preferably carry one, two, three, four or five identical or different halogen atoms. The term halogen represents in each case fluorine, chlorine, bromine or iodine. Examples of other meanings are:

$C_1$–$C_4$-alkyl: $CH_3$, $C_2H_5$, n-propyl, $CH(CH_3)_2$, n-butyl, $CH(CH_3)$—$C_2H_5$, $CH_2$—$CH(CH_3)_2$ and $C(CH_3)_3$;

$C_1$–$C_4$-haloalkyl: a $C_1$–$C_4$-alkyl radical as mentioned above which is partially or fully substituted by fluorine, chlorine, bromine and/or iodine, i.e. for example $CH_2F$, $CHF_2$, $CF_3$, $CH_2Cl$, dichloromethyl, trichloromethyl, chlorofluoromethyl, dichlorofluoromethyl, chlorodifluoro-methyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-fluoromethyl-2-fluoroethyl, 1-chloromethyl-2-chloroethyl, 1-bromomethyl-2-bromoethyl, 4-fluorobutyl, 4-chlorobutyl, 4-bromobutyl and nonafluorobutyl;

$C_1$–$C_6$-alkyl: $C_1$–$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$–$C_6$-haloalkyl: a $C_1$–$C_6$-alkyl radical as mentioned above which is partially or fully substituted by fluorine, chlorine, bromine and/or iodine, i.e. for example one of the radicals mentioned under $C_1$–$C_4$-haloalkyl, and also 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl;

phenyl-$C_1$–$C_4$-alkyl: benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-phenylmethyleth-1-yl, 1-phenylmethyl-1-methyleth-1-yl or 1-phenylmethylprop-1-yl, preferably benzyl or 2-phenylethyl;

heterocyclyl-$C_1$–$C_4$-alkyl: heterocyclylmethyl, 1-heterocyclylethyl, 2-heterocyclylethyl, 1-heterocyclylprop-1-yl, 2-heterocyclylprop-1-yl, 3-heterocyclylprop-1-yl, 1-hetero-cyclylbut-1-yl, 2-heterocyclylbut-1-yl, 3-heterocyclylbut-1-yl, 4-heterocyclylbut-1-yl, 1-heterocyclylbut-2-yl, 2-heterocyclylbut-2-yl, 3-heterocyclylbut-2-yl, 3-hetero-cyclylbut-2-yl, 4-heterocyclylbut-2-yl, 1-heterocyclylmethyleth-1-yl, 1-heterocyclylmethyl-1-methyleth-1-yl or 1-heterocyclylmethylprop-1-yl, preferably heterocyclylmethyl or 2-heterocyclylethyl;

cyano-$C_1$–$C_4$-alkyl: $CH_2CN$, 1-cyanoethyl, 2-cyanoethyl, 1-cyanoprop-1-yl, 2-cyanoprop-1-yl, 3-cyanoprop-1-yl, 1-cyanobut-1-yl, 2-cyanobut-1-yl, 3-cyanobut-1-yl, 4-cyanobut-1-yl, 1-cyanobut-2-yl, 2-cyanobut-2-yl, 3-cyanobut-2-yl, 4-cyanobut-2-yl, 1-($CH_2CN$)eth-1-yl, 1-($CH_2CN$)-1-($CH_3$)eth-1-yl or 1-($CH_2CN$)prop-1-yl;

$C_1$–$C_4$-alkoxy: $OCH_3$, $OC_2H_5$, n-propoxy, $OCH(CH_3)_2$, n-butoxy, $OCH(CH_3)$—$C_2H_5$, $OCH_2$—$CH(CH_3)_2$ or $OC(CH_3)_3$, preferably $OCH_3$, $OC_2H_5$, or $OCH(CH_3)_2$;

$C_1$–$C_4$-haloalkoxy: a $C_1$–$C_4$-alkoxy radical as mentioned above which is partially or fully substituted by fluorine, chlorine, bromine and/or iodine, i.e. for example $OCH_2F$, $OCHF_2$, $OCF_3$, $OCH_2Cl$, $OCH(Cl)_2$, $OC(Cl)_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy, preferably $OCHF_2$, $OCF_3$, dichlorofluoromethoxy, chlorodifluoromethoxy or 2,2,2-trifluoroethoxy;

$C_1$–$C_6$-alkylthio: $SCH_3$, $SC_2H_5$, n-propylthio, $SCH(CH_3)_2$, n-butylthio, $SCH(CH_3)$—$C_2H_5$, $SCH_2$—$CH(CH_3)_2$ or $SC(CH_3)_3$, preferably $SCH_3$ or $SC_2H_5$;

$C_1$–$C_4$-haloalkylthio: a $C_1$–$C_4$-alkylthio radical as mentioned above which is partially or fully substituted by fluorine, chlorine, bromine and/or iodine, i.e. for example $SCH_2F$, $SCHF_2$, $SCH_2Cl$, $SCH(Cl)_2$, $SC(Cl)_3$, $SCF_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, $SC_2F_5$, 2-fluoropropylthio, 3-fluoropropylthio, 2,2-difluoropropylthio-2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or $SCF_2$—$CF_2$—$C_2F_5$, preferably $SCHF_2$, $SCF_3$, dichlorofluoromethylthio, chlorodifluoromethylthio or 2,2,2-trifluoroethylthio;

$C_1$–$C_4$-alkoxy-$C_1$–$C_4$-alkyl: $C_1$–$C_4$-alkyl which is substituted by $C_1$–$C_4$-alkoxy as mentioned above, i.e. for example $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, CH$_2$—OC(CH$_3$)$_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, preferably CH$_2$—OCH$_3$, CH$_2$—OC$_2$H$_5$, 2-methoxyethyl or 2-ethoxyethyl;

C$_1$–C$_4$-alkylthio-C$_1$–C$_4$-alkyl: C$_1$–C$_4$-alkyl which is substituted by C$_1$–C$_4$-alkylthio as mentioned above, i.e. for example CH$_2$—SCH$_3$, CH$_2$—SC$_2$H$_5$, n-propylthiomethyl, CH$_2$—SCH(CH$_3$)$_2$, n-butylthiomethyl, (1-methylpropylthio)methyl, (2-methylpropylthio)methyl, CH$_2$—SC(CH$_3$)$_3$, 2-(methylthio)ethyl, 2-(ethylthio)ethyl, 2-(n-propylthio)ethyl, 2-(1-methylethylthio)ethyl, 2-(n-butylthio)ethyl, 2-(1-methylpropylthio)ethyl, 2-(2-methylpropylthio)ethyl, 2-(1,1-dimethylethylthio)ethyl, 2-(methylthio)propyl, 2-(ethylthio)propyl, 2-(n-propylthio)-propyl, 2-(1-methylethylthio)propyl, 2-(n-butylthio)propyl, 2-(1-methylpropylthio)propyl, 2-(2-methylpropylthio)propyl, 2-(1,1-dimethylethylthio)propyl, 3-(methylthio)propyl, 3-(ethylthio)propyl, 3-(n-propylthio)propyl, 3-(1-methylethylthio)propyl, 3-(n-butylthio)propyl, 3-(1-methylpropylthio)propyl, 3-(2-methylpropylthio)propyl, 3-(1,1-dimethylethylthio)propyl, 2-(methylthio)butyl, 2-(ethylthio)butyl, 2-(n-propylthio)butyl, 2-(1-methylethylthio)butyl, 2-(n-butylthio)butyl, 2-(1-methylpropylthio)butyl, 2-(2-methylpropylthio)butyl, 2-(1,1-dimethylethylthio)butyl, 3-(methylthio)butyl, 3-(ethylthio)butyl, 3-(n-propylthio)butyl, 3-(1-methylethylthio)butyl, 3-(n-butylthio)butyl, 3-(1-methylpropylthio)butyl, 3-(2-methylpropylthio)butyl, 3-(1,1-dimethylethylthio)butyl, 4-(methylthio)butyl, 4-(ethylthio)butyl, 4-(n-propylthio)butyl, 4-(1-methylethylthio)butyl, 4-(n-butylthio)butyl, 4-(1-methylpropylthio)butyl, 4-(2-methylpropylthio)butyl or 4-(1,1-dimethylethylthio)butyl, preferably CH$_2$—SCH$_3$, CH$_2$—SC$_2$H$_5$, 2-(SCH$_3$)ethyl or 2-(SC$_2$H$_5$)ethyl;

(C$_1$–C$_4$-alkoxy)carbonyl-C$_1$–C$_4$-alkyl: C$_1$–C$_4$-alkyl which is substituted by (C$_1$–C$_4$-alkoxy)carbonyl as mentioned above, i.e. for example CH$_2$—CO—OCH$_3$, CH$_2$—CO—OC$_2$H$_5$, n-propoxycarbonylmethyl, CH$_2$—CO—OCH(CH$_3$)$_2$, n-butoxycarbonylmethyl, CH$_2$—CO—OCH(CH$_3$)—C$_2$H$_5$, CH$_2$—CO—OCH$_2$—CH(CH$_3$)$_2$, CH$_2$—CO—OC(CH$_3$)$_3$, 1-(methoxycarbonyl)ethyl, 1-(ethoxycarbonyl)ethyl, 1-(n-propoxycarbonyl)ethyl, 1-(1-methylethoxycarbonyl)ethyl, 1-(n-butoxycarbonyl)ethyl, 2-(methoxycarbonyl)ethyl, 2-(ethoxycarbonyl)ethyl, 2-(n-propoxycarbonyl)ethyl, 2-(1-methylethoxycarbonyl)ethyl, 2-(n-butoxycarbonyl)ethyl, 2-(1-methylpropoxycarbonyl)ethyl, 2-(2-methylpropoxycarbonyl)ethyl, 2-(1,1-dimethylethoxycarbonyl)ethyl, 2-(methoxycarbonyl)propyl, 2-(ethoxycarbonyl)propyl, 2-(n-propoxycarbonyl)propyl, 2-(1-methylethoxycarbonyl)propyl, 2-(n-butoxycarbonyl)propyl, 2-(1-methylpropoxycarbonyl)propyl, 2-(2-methylpropoxycarbonyl)propyl, 2-(1,1-dimethylethoxycarbonyl)propyl, 3-(methoxycarbonyl)propyl, 3-(ethoxycarbonyl)propyl, 3-(n-propoxycarbonyl)propyl, 3-(1-methylethoxycarbonyl)propyl, 3-(n-butoxycarbonyl)propyl, 3-(1-methylpropoxycarbonyl)propyl, 3-(2-methylpropoxycarbonyl)propyl, 3-(1,1-dimethylethoxycarbonyl)propyl, 2-(methoxycarbonyl)butyl, 2-(ethoxycarbonyl)butyl, 2-(n-propoxycarbonyl)butyl, 2-(1-methylethoxycarbonyl)butyl, 2-(n-butoxycarbonyl)butyl, 2-(1-methylpropoxycarbonyl)butyl, 2-(2-methylpropoxycarbonyl)butyl, 2-(1,1-dimethylethoxycarbonyl)butyl, 3-(methoxycarbonyl)butyl, 3-(ethoxycarbonyl)butyl, 3-(n-propoxycarbonyl)butyl, 3-(1-methylethoxycarbonyl)butyl, 3-(n-butoxycarbonyl)butyl, 3-(1-methylpropoxycarbonyl)butyl, 3-(2-methylpropoxycarbonyl)butyl, 3-(1,1-dimethylethoxycarbonyl)butyl, 4-(methoxycarbonyl)butyl, 4-(ethoxycarbonyl)butyl, 4-(n-propoxycarbonyl)butyl, 4-(1-methylethoxycarbonyl)butyl, 4-(n-butoxycarbonyl)butyl, 4-(1-methylpropoxycarbonyl)butyl, 4-(2-methylpropoxycarbonyl)butyl or 4-(1,1-dimethylethoxycarbonyl)butyl, preferably CH$_2$—CO—OCH$_3$, CH$_2$—CO—OC$_2$H$_5$, 1-(methoxycarbonyl)ethyl or 1-(ethoxycarbonyl)ethyl;

C$_1$–C$_4$-alkylsulfinyl: SO—CH$_3$, SO—C$_2$H$_5$, SO—CH$_2$—C$_2$H$_5$, SO—CH(CH$_3$)$_2$, n-butylsulfinyl, SO—CH(CH$_3$)—C$_2$H$_5$, SO—CH$_2$—CH(CH$_3$)$_2$ or SO—C(CH$_3$)$_3$, preferably SO—CH$_3$ or SO—C$_2$H$_5$;

C$_1$–C$_4$-haloalkylsulfinyl: a C$_1$–C$_4$-alkylsulfinyl radical as mentioned above which is partially or fully substituted by fluorine, chlorine, bromine and/or iodine, i.e. for example SO—CH$_2$F, SO—CHF$_2$, SO—CF$_3$, SO—CH$_2$Cl, SO—CH(Cl)$_2$, SO—C(Cl)$_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl, SO—C$_2$F$_5$, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, SO—CH$_2$—C$_2$F$_5$, SO—CF$_2$—C$_2$F$_5$, 1-(CH$_2$F)-2-fluoroethylsulfinyl, 1-(CH$_2$Cl)-2-chloroethylsulfinyl, 1-(CH$_2$Br)-2-bromoethylsulfinyl, 4-fluorobutylsulfinyl, 4-chlorobutylsulfinyl, 4-bromobutylsulfinyl or nonafluorobutylsulfinyl, preferably SO—CF$_3$, SO—CH$_2$Cl or 2,2,2-trifluoroethylsulfinyl;

C$_1$–C$_4$-alkylsulfonyl: SO$_2$—CH$_3$, SO$_2$—C$_2$H$_5$, SO$_2$—CH$_2$—C$_2$H$_5$, SO$_2$—CH(CH$_3$)$_2$, n-butylsulfonyl, SO$_2$—CH(CH$_3$)—C$_2$H$_5$, SO$_2$—CH$_2$—CH(CH$_3$)$_2$ or SO$_2$-C(CH$_3$)$_3$, preferably SO$_2$—CH$_3$ or SO$_2$—C$_2$H$_5$;

C$_1$–C$_4$-haloalkylsulfonyl: a C$_1$–C$_4$-alkylsulfonyl radical as mentioned above which is partially or fully substituted by fluorine, chlorine, bromine and/or iodine, i.e. for example SO$_2$—CH$_2$F, SO$_2$—CHF$_2$, SO$_2$-CF$_3$, SO$_2$—CH$_2$Cl, SO$_2$—CH(Cl)$_2$, SO$_2$—C(Cl)$_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, SO$_2$—C$_2$F$_5$, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, SO$_2$—CH$_2$—C$_2$F$_5$, SO$_2$—CF$_2$—C$_2$F$_5$, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl or nonafluorobutylsulfonyl, preferably SO$_2$—CF$_3$, SO$_2$—CH$_2$Cl or 2,2,2-trifluoroethylsulfonyl;

C$_2$–C$_6$-alkenyl: ethenyl, prop-1-en-1-yl, allyl, 1-methylethenyl, 1-buten-1-yl, 1-buten-2-yl, 1-buten-3-yl, 2-buten-1-yl, 1-methylprop-1-en-1-yl, 2-methylprop-1-en-1-yl, 1-methyl-prop-2-en-1-yl, 2-methyl-prop-2-en-1-yl, n-penten-1-yl, n-penten-2-yl, n-penten-3-yl, n-penten-4-yl, 1-methyl-but-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

C$_2$–C$_6$-haloalkenyl: C$_2$–C$_6$-alkenyl as mentioned above which is partially or fully substituted by fluorine, chlorine, bromine and/or iodine, i.e. for example 2-chloroethenyl, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl and 2,3-dibromobut-2-enyl;

C$_2$–C$_6$-alkynyl: ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, preferably prop-2-yn-1-yl;

C$_3$–C$_8$-cycloalkyl: cyclopropyl, cyclobutyl, cyclopentyl, cyclohexyl, cycloheptyl or cyclooctyl;

C$_3$–C$_8$-cycloalkyl-C$_1$–C$_4$-alkyl: cyclopropylmethyl, 1-cyclopropylethyl, 2-cyclopropylethyl, 1-cyclopropylprop-1-yl, 2-cyclopropylprop-1-yl, 3-cyclopropylprop-1-yl, 1-cyclopropylbut-1-yl, 2-cyclopropylbut-1-yl, 3-cyclopropylbut-1-yl, 4-cyclopropylbut-1-yl, 1-cyclopropylbut-2-yl, 2-cyclopropylbut-2-yl, 3-cyclopropylbut-2-yl, 3-cyclopropylbut-2-yl, 4-cyclopropylbut-2-yl, 1-(cyclopropylmethyl)eth-1-yl, 1-(cyclopropylmethyl)-1-(methyl)eth-1-yl, 1-(cyclopropylmethyl)prop-1-yl, cyclobutylmethyl, 1-cyclobutylethyl, 2-cyclobutylethyl, 1-cyclobutylprop-1-yl, 2-cyclobutylprop-1-yl, 3-cyclobutylprop-1-yl, 1-cyclobutylbut-1-yl, 2-cyclobutylbut-1-yl, 3-cyclobutylbut-1-yl, 4-cyclobutylbut-1-yl, 1-cyclobutylbut-2-yl, 2-cyclobutylbut-2-yl, 3-cyclobutylbut-2-yl, 3-cyclobutylbut-2-yl, 4-cyclobutylbut-2-yl, 1-(cyclobutylmethyl)eth-1-yl, 1-(cyclobutylmethyl)-1-(methyl)eth-1-yl, 1-(cyclobutylmethyl)prop-1-yl, cyclopentylmethyl, 1-cyclopentylethyl, 2-cyclopentylethyl, 1-cyclopentylprop-1-yl, 2-cyclopentylprop-1-yl, 3-cyclopentylprop-1-yl, 1-cyclopentylbut-1-yl, 2-cyclopentylbut-1-yl, 3-cyclopentylbut-1-yl, 4-cyclopentylbut-1-yl, 1-cyclopentylbut-2-yl, 2-cyclopentylbut-2-yl, 3-cyclopentylbut-2-yl, 3-cyclopentylbut-2-yl, 4-cyclopentylbut-2-yl, 1-(cyclopentylmethyl)eth-1-yl, 1-(cyclopentylmethyl)1-(methyl)eth-1-yl, 1-(cyclopentylmethyl)prop-1-yl, cyclohexylmethyl, 1-cyclohexylethyl, 2-cyclohexylethyl, 1-cyclohexylprop-1-yl, 2-cyclohexylprop-1-yl, 3-cyclohexylprop-1-yl, 1-cyclohexylbut-1-yl, 2-cyclohexylbut-1-yl, 3-cyclohexylbut-1-yl, 4-cyclohexylbut-1-yl, 1-cyclohexylbut-2-yl, 2-cyclohexylbut-2-yl, 3-cyclohexylbut-2-yl, 3-cyclohexylbut-2-yl, 4-cyclohexylbut-2-yl, 1-(cyclohexylmethyl)eth-1-yl, 1-(cyclohexylmethyl)-1-(methyl)eth-1-yl, 1-(cyclohexylmethyl)prop-1-yl, cycloheptylmethyl, 1-cycloheptylethyl, 2-cycloheptylethyl, 1-cycloheptylprop-1-yl, 2-cycloheptylprop-1-yl, 3-cycloheptylprop-1-yl, 1-cycloheptylbut-1-yl, 2-cycloheptylbut-1-yl, 3-cycloheptylbut-1-yl, 4-cycloheptylbut-1-yl, 1-cycloheptylbut-2-yl, 2-cycloheptylbut-2-yl, 3-cycloheptylbut-2-yl, 3-cycloheptylbut-2-yl, 4-cycloheptylbut-2-yl, 1-(cycloheptylmethyl)eth-1-yl, 1-(cycloheptylmethyl)-1-(methyl)eth-1-yl, 1-(cycloheptylmethyl)prop-1-yl, cyclooctylmethyl, 1-cyclooctylethyl, 2-cyclooctylethyl, 1-cyclooctylprop-1-yl, 2-cyclooctylprop-1-yl, 3-cyclooctylprop-1-yl, 1-cyclooctylbut-1-yl, 2-cyclooctylbut-1-yl, 3-cyclooctylbut-1-yl, 4-cyclooctylbut-1-yl, 1-cyclooctylbut-2-yl, 2-cyclooctylbut-2-yl, 3-cyclooctylbut-2-yl, 3-cyclooctylbut-2-yl, 4-cyclooctylbut-2-yl, 1-(cyclooctylmethyl)eth-1-yl, 1-(cyclooctylmethyl)-1-(methyl)eth-1-yl or 1-(cyclooctylmethyl)prop-1-yl, preferably cyclopropylmethyl, cyclobutylmethyl, cyclopentylmethyl or cyclohexylmethyl;

4- to 7-membered heterocyclyl is to be understood as meaning both saturated, partially or fully unsaturated and aromatic heterocycles having one, two or three hetero atoms, where the hetero atoms are selected from nitrogen, oxygen and sulfur. Preferred heterocyclyl is 5- to 7-membered.

Examples of saturated heterocycles are: oxetan-2-yl, oxetan-3-yl, thietan-2-yl, thietan-3-yl, azetidin-1-yl, azetidin-2-yl, azetidin-3-yl, tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-2-yl, 1,3-dithiepan-2-yl, 1,3-dithiepan-2-yl, 1,4-dioxepan-2-yl, 1,4-dioxepan-7-yl, hexahydroazepin-1-yl, hexahydroazepin-2-yl, hexahydroazepin-3-yl, hexahydroazepin-4-yl, hexahydro-1,3-diazepin-1-yl, hexahydro-1,3-diazepin-2-yl, hexahydro-1,3-diazepin-4-yl, hexahydro-1,4-diazepin-1-yl and hexahydro-1,4-diazepin-2-yl.

Examples of unsaturated heterocycles are: dihydrofuran-2-yl, 1,2-oxazolin-3-yl, 1,2-oxazolin-5-yl, 1,3-oxazolin-2-yl.

Examples of aromatic heterocyclyl are the 5- and 6-membered aromatic heterocyclic radicals, for example furyl, such as 2-furyl and 3-furyl, thienyl, such as 2-thienyl and 3-thienyl, pyrrolyl such as 2-pyrrolyl and 3-pyrrolyl, isoxazolyl, such as 3-isoxazolyl, 4-isoxazolyl and 5-isoxazolyl, isothiazolyl, such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-oxazolyl, 4-oxazolyl and 5-oxazolyl, thiazolyl, such as 2-thiazolyl, 4-thiazolyl and 5-thiazolyl, imidazolyl, such as 2-imidazolyl and 4-imidazolyl, oxadiazolyl, such as 1,2,4-oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazolyl, such as 1,2,4-triazol-1-yl, 1,2,4-triazol-3-yl and 1,2,4-triazol-4-yl, pyridinyl, such as 2-pyridinyl, 3-pyridinyl and 4-pyridinyl, pyridazinyl, such as 3-pyridazinyl and 4-pyridazinyl, pyrimidinyl, such as 2-pyrimidinyl, 4-pyrimidinyl and 5-pyrimidinyl, furthermore 2-pyrazinyl, 1,3,5-triazin-2-yl and 1,2,4-triazin-3-yl, in particular pyridyl, pyrimidyl, furanyl and thienyl.

Suitable transition metal compounds are, for example, compounds of manganese, rhenium, iron, ruthenium, osmium, cobalt, rhodium, iridium, nickel, palladium, platinum, copper, silver or gold, in particular of copper, manganese, palladium, cobalt or nickel. Examples of compounds of the abovementioned transition metals are their halides, such as $MnCl_2$, $MnBr_2$, $MnI_2$, $ReCl_3$, $ReBr_3$, $ReI_3$, $ReCl_4$, $ReBr_4$, $ReI_4$, $ReCl_5$, $ReBr_5$, $ReCl_6$, $FeCl_2$, $FeBr_2$, $FeI_2$, $FeCl_3$, $FeBr_3$, $RuCl_2$, $RuBr_2$, $RuI_2$, $RuCl_3$, $RuBr_3$, $RuI_3$, $OsI$, $OSI2$, $OsCl_3$, $OsBr_3$, $OSI3$, $OsCl_4$, $OsBr_4$, $OsCl_5$, $CoCl_2$, $CoBr_2$, $CoI_2$, $RhCl_3$, $RhBr_3$, $RhI_3$, $IrCl_3$, $IrBr_3$, $IrI_3$, $NiCl_2$, $NiBr_2$, $NiI_2$, $PdCl_2$, $PdBr_2$, $PdI_2$, $PtCl_2$, $PtBr_2$, $PtI_2$, $PtCl_3$, $PtBr_3$, $PtI_3$, $PtCl_4$, $PtBr_4$, $PtI_4$, $CuCl$, $CuBr$, $CuI$, $CuCl_2$, $CuBr_2$, $AgCl$, $AgBr$, $AgI$, $AuCl$, $AuI$, $AuCl_3$, $AuBr_3$ and oxides and sulfides thereof, e.g. $Cu_2S$ and $Cu_2O$. In the process according to the invention, it is also possible to employ the transition metal in question per se, if it is converted under the reaction conditions into the actual catalytically active transition metal compound.

In a preferred embodiment of the process according to the invention, the transition metal used is a copper(II) and/or a copper(I) compound, in particular a copper(I) halide, for example copper(I) chloride, copper(I) bromide or copper(I) iodide.

In the process according to the invention, in addition to the transition metal compound which catalyzes the cyclization of II to I, it is also possible to use a cocatalyst, the cocatalyst being a compound which is a complex ligand for the transition metal in question. Examples of cocatalysts are phosphines, such as triphenylphosphine, tri-o-tolylphosphine, tri-n-butylphosphine, 1,2-bis(diphenylphosphino)ethane, 1,3-bis(diphenylphosphino)propane, phosphites, such as trimethyl phosphite, triethyl phosphite or triisopropyl phosphite, sulfides, such as dimethyl sulfide, and also cyanide or carbon monoxide. If desired, the cocatalyst is generally employed in at least equimolar amounts, based on the transition metal.

The transition metal compounds can also be employed as complex compounds which preferably have one or more of the abovementioned cocatalysts as ligands. Examples of such compounds are $[NiCl_2(PPh_3)_2]$, $[Pd(PPh_3)_4]$, $[PdCl_2(PPh_3)_2]$, $[PdCl_2(dppe)]$, $[PdCl_2(dppp)]$, $[PdCl_2(dppb)]$, $[CuBr(S(CH_3)_2)]$, $[CuI(P(OC_2H_5)_3)]$, $[CuI(P(OCH_3)_3)]$, $[CuCl(PPh_3)_3]$ or $[AuCl(P(OC_2H_5)_3)]$.

If desired, the transition metal compounds can also be immobilized on an inert support, for example on active carbon, silica gel, alumina, or on an insoluble polymer, for example a styrene/divinylbenzene copolymer.

In the process according to the invention, the transition metal compounds can be employed both in an equimolar amount, based on the compound II, and in substoichiometric or superstoichiometric amounts. The molar ratio of transition metal to the compound II used is usually in the range from 0.01:1 to 5:1, preferably in the range from 0.02:1 to 2:1, and in particular in the range from 0.05:1 to about 1:1.5. In a preferred variant, an equimolar amount of transition metal compound is used, i.e. the molar ratio of transition metal to the compound II used is about 1:1. However, the transition metal compound is particularly preferably employed in a catalytic, i.e. substoichiometric, amount. The molar ratio of transition metal to the compound II used is then <1:1. In this variant, the molar ratio of transition metal compound to the compound II used is particularly preferably in the range from 0.05:1 to 0.8:1, for example from 0.1:1 to 0.3:1.

According to the invention, the process is carried out in the presence of a base. Suitable bases are, in principle, all basic compounds which are capable of deprotonating the amide group in II. Preference is given to bases, such as alkoxides, amides, hydrides, hydroxides, bicarbonates and carbonates of alkali metals or alkaline earth metals, in particular of lithium, potassium, sodium, cesium or calcium. Examples of suitable bases are the sodium or potassium alkoxides of methanol, ethanol, n-propanol, isopropanol, n-butanol and tert-butanol, furthermore sodium hydride and potassium hydride, calcium hydride, sodium amide, potassium amide, sodium carbonate, potassium carbonate, cesium carbonate, sodium bicarbonate, potassium bicarbonate, sodium hydroxide, potassium hydroxide and lithium hydroxide. In a preferred embodiment of the process according to the invention, the base used is sodium hydride. In another embodiment of the process according to the invention, which is particularly preferred, the base used is potassium carbonate and/or potassium bicarbonate. The base can be employed in substoichiometric, superstoichiometric or equimolar amounts. Preference is given to using at least an equimolar amount of base, based on the compound II. In particular, the molar ratio of base (calculated as base equivalents) to compound II is in the range from 1:1 to 1:5 and particularly preferably in the range from 1:1 to 1:1.5.

The conversion of II into I is preferably carried out in an organic solvent. Suitable solvents are, in principle, all organic solvents which are inert under the reaction conditions. These are, for example, hydrocarbons, such as hexane or toluene, halogenated hydrocarbons, such as 1,2-dichloroethane or chlorobenzene, ethers, such as dioxane, tetrahydrofuran (THF), methyl tert-butyl ether, dimethoxyethane, diethylene glycol dimethyl ether and triethylene glycol dimethyl ether, aprotic polar solvents, for example organic amides, such as dimethylformamide (DMF), N-methylpyrrolidone (NMP), N,N-dimethylacetamide (DMA), dimethyl sulfoxide (DMSO), organic nitriles, such as acetonitrile or propionitrile, and also tertiary nitrogen bases, for example pyridine. It is, of course, also possible to use mixtures of the solvents mentioned. Preference is given to using aprotic polar solvents such as DMSO, DMF, NMP, DMA, acetonitrile, propionitrile, pyridine, dimethoxyethane, diethylene glycol dimethyl ether and triethylene glycol dimethyl ether, or mixtures thereof.

According to its nature, the reaction temperature depends on the reactivity of the compound II in question. In general, the reaction temperature is not below room temperature. The conversion of II into I is preferably carried out at temperatures below 200° C. Frequently, the reaction is carried out at elevated temperature, for example above 50° C., in particular above 70° C. and particularly preferably above 100° C. The reaction is preferably carried out at temperatures below 180° C. and in particular below 160° C.

Work-up of the reaction product to afford the target compound I can be carried out by the methods which are customary for this purpose. In general, the mixture is initially worked up by extraction, or the solvent used is removed by customary methods, for example distillatively.

It is also possible to extract the target compound I from the reaction mixture, after dilution of the reaction mixture with water, using a volatile organic solvent which for its part is removed again distillatively. It is also possible to precipitate the target compound from the reaction mixture by adding water. This gives a crude product which contains the product of value I. For further purification, it is possible to use the customary processes, such as crystallization or chromatography, for example over alumina or silica gel. It is likewise possible to chromatograph the substances obtainable by the process over optically active adsorbates, to obtain the pure isomers.

$R^3$ in formula II is preferably a radical which is different from hydrogen. In the process according to the invention, preference is given to using those compounds of the formula II in which the variables $R^1$ to $R^6$ independently of one another, but preferably in combination with one another, have the meanings given below:

$R^1$ is hydrogen or $C_1$–$C_4$-alkyl, in particular methyl or ethyl;

$R^2$ is cyano, difluoromethoxy, trifluoromethyl or methylsulfonyl;

$R^3$ is halogen;

$R^4$ is halogen;

$R^5$ is fluorine, chlorine or cyano;

$R^6$ is hydrogen, $C_1$–$C_4$-alkyl, $C_1$–$C_4$-haloalkyl, $C_2$–$C_4$-alkenyl, $C_2$–$C_4$-haloalkenyl, $C_2$–$C_4$-alkynyl, $C_1$–$C_4$-alkoxy-$C_1$–$C_4$-alkyl, $C_1$–$C_4$-alkoxycarbonyl-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl, 4- to 7-membered heterocyclyl or heterocyclyl-$C_1$–$C_4$-alkyl, where the phenyl ring, the cycloalkyl ring and the heterocyclyl ring can be unsubstituted or may carry one or two substituents, selected from the group consisting of cyano, halogen, $C_1$–$C_4$-alkyl, $C_1$–$C_4$-haloalkyl and $C_1$–$C_4$-alkoxy. Examples of preferred meanings of $R^6$ are given in Table 1.

Amongst these, particular preference is given to those compounds II in which $R^1$ is methyl. $R^2$ is in particular trifluoromethyl and particularly preferably difluoromethoxy. $R^3$ is in particular chlorine or bromine. $R^4$ is in particular fluorine or chlorine. $R^5$ is in particular chlorine. $R^6$ is in particular hydrogen, $C_1$–$C_4$-alkyl, $C_1$–$C_4$-alkoxy-$C_1$–$C_4$-alkyl, $C_3$–$C_8$-cycloalkyl, $C_3$–$C_8$-cycloalkyl-$C_1$–$C_4$-alkyl, phenyl or phenyl-$C_1$–$C_4$-alkyl.

Examples of particularly preferred compounds of the formula II are the bromoanilides of the formulae IIa and IIc and the iodoanilides of the formulae IIb and IId in which $R^1$ is $CH_3$, $R^2$ is $OCHF_2$ or $CF_3$ and $R^5$ is Cl and the variables $R^3$, $R^4$ and $R^6$ in each case correspond to one row of Table 1 (compounds IIa.1–IIa.116, compounds IIb.1–IIb.116, compounds IIc.1–IIc.116 and compounds IId.1–IId.116).

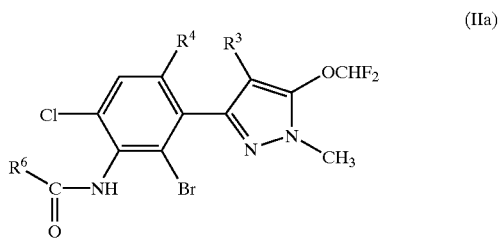

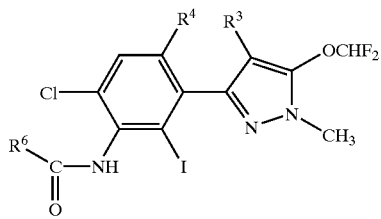

(IIb)

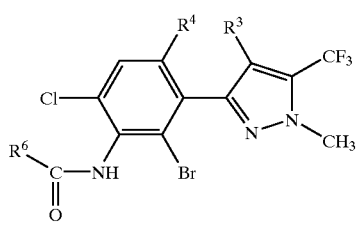

(IIc)

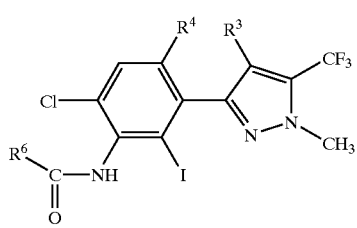

(IId)

TABLE 1

| No. | R³ | R⁴ | R⁶ |
|---|---|---|---|
| 1 | Cl | F | H |
| 2 | Cl | Cl | H |
| 3 | Br | F | H |
| 4 | Br | Cl | H |
| 5 | Cl | F | CH₃ |
| 6 | Cl | Cl | CH₃ |
| 7 | Br | F | CH₃ |
| 8 | Br | Cl | CH₃ |
| 9 | Cl | F | C₂H₅ |
| 10 | Cl | Cl | C₂H₅ |
| 11 | Br | F | C₂H₅ |
| 12 | Br | Cl | C₂H₅ |
| 13 | Cl | F | n-C₃H₇ |
| 14 | Cl | Cl | n-C₃H₇ |
| 15 | Br | F | n-C₃H₇ |
| 16 | Br | Cl | n-C₃H₇ |
| 17 | Cl | F | CH(CH₃)₂ |
| 18 | Cl | Cl | CH(CH₃)₂ |
| 19 | Br | F | CH(CH₃)₂ |
| 20 | Br | Cl | CH(CH₃)₂ |
| 21 | Cl | F | n-C₄H₉ |
| 22 | Cl | Cl | n-C₄H₉ |
| 23 | Br | F | n-C₄H₉ |
| 24 | Br | Cl | n-C₄H₉ |
| 25 | Cl | F | CH₂—CH(CH₃)₂ |
| 26 | Cl | Cl | CH₂—CH(CH₃)₂ |
| 27 | Br | F | CH₂—CH(CH₃)₂ |
| 28 | Br | Cl | CH₂—CH(CH₃)₂ |
| 29 | Cl | F | CH(CH₃)—C₂H₅ |
| 30 | Cl | Cl | CH(CH₃)—C₂H₅ |
| 31 | Br | F | CH(CH₃)—C₂H₅ |
| 32 | Br | Cl | CH(CH₃)—C₂H₅ |
| 33 | Cl | F | C(CH₃)₃ |
| 34 | Cl | Cl | C(CH₃)₃ |
| 35 | Br | F | C(CH₃)₃ |
| 36 | Br | Cl | C(CH₃)₃ |
| 37 | Cl | F | CH₂—Cl |
| 38 | Cl | Cl | CH₂—Cl |
| 39 | Br | F | CH₂—Cl |
| 40 | Br | Cl | CH₂—Cl |
| 41 | Cl | F | CH₂—F |
| 42 | Cl | Cl | CH₂—F |
| 43 | Br | F | CH₂—F |
| 44 | Br | Cl | CH₂—F |
| 45 | Cl | F | CF₃ |
| 46 | Cl | Cl | CF₃ |
| 47 | Br | F | CF₃ |
| 48 | Br | Cl | CF₃ |
| 49 | Cl | F | CH=CH₂ |
| 50 | Cl | Cl | CH=CH₂ |
| 51 | Br | F | CH=CH₂ |
| 52 | Br | Cl | CH=CH₂ |
| 53 | Cl | F | CH=CH—CH₃ |
| 54 | Cl | Cl | CH=CH—CH₃ |
| 55 | Br | F | CH=CH—CH₃ |
| 56 | Br | Cl | CH=CH—CH₃ |
| 57 | Cl | F | CH=CH—Cl |
| 58 | Cl | Cl | CH=CH—Cl |
| 59 | Br | F | CH=CH—Cl |
| 60 | Br | Cl | CH=CH—Cl |
| 61 | Cl | F | C≡CH |
| 62 | Cl | Cl | C≡CH |
| 63 | Br | F | C≡CH |
| 64 | Br | Cl | C≡CH |
| 65 | Cl | F | C≡C—CH₃ |
| 66 | Cl | Cl | C≡C—CH₃ |
| 67 | Br | F | C≡C—CH₃ |
| 68 | Br | Cl | C≡C—CH₃ |
| 69 | Cl | F | CH₂—OCH₃ |
| 70 | Cl | Cl | CH₂—OCH₃ |
| 71 | Br | F | CH₂—OCH₃ |
| 72 | Br | Cl | CH₂—OCH₃ |
| 73 | Cl | F | CH₂—OC₂H₅ |
| 74 | Cl | Cl | CH₂—OC₂H₅ |
| 75 | Br | F | CH₂—OC₂H₅ |
| 76 | Br | Cl | CH₂—OC₂H₅ |
| 77 | Cl | F | CH₂—CH₂—OCH₃ |
| 78 | Cl | Cl | CH₂—CH₂—OCH₃ |
| 79 | Br | F | CH₂—CH₂—OCH₃ |
| 80 | Br | Cl | CH₂—CH₂—OCH₃ |
| 81 | Cl | F | CH₂—CH₂—OC₂H₅ |
| 82 | Cl | Cl | CH₂—CH₂—OC₂H₅ |
| 83 | Br | F | CH₂—CH₂—OC₂H₅ |
| 84 | Br | Cl | CH₂—CH₂—OC₂H₅ |
| 85 | Cl | F | cyclopropyl |
| 86 | Cl | Cl | cyclopropyl |
| 87 | Br | F | cyclopropyl |
| 88 | Br | Cl | cyclopropyl |
| 89 | Cl | F | cyclopentyl |
| 90 | Cl | Cl | cyclopentyl |
| 91 | Br | F | cyclopentyl |
| 92 | Br | Cl | cyclopentyl |
| 93 | Cl | F | cyclohexyl |
| 94 | Cl | Cl | cyclohexyl |
| 95 | Br | F | cyclohexyl |
| 96 | Br | Cl | cyclohexyl |
| 97 | Cl | F | CH₂-cyclopropyl |
| 98 | Cl | Cl | CH₂-cyclopropyl |
| 99 | Br | F | CH₂-cyclopropyl |
| 100 | Br | Cl | CH₂-cyclopropyl |
| 101 | Cl | F | phenyl |
| 102 | Cl | Cl | phenyl |
| 103 | Br | F | phenyl |
| 104 | Br | Cl | phenyl |
| 105 | Cl | F | benzyl |
| 106 | Cl | Cl | benzyl |
| 107 | Br | F | benzyl |
| 108 | Br | Cl | benzyl |
| 109 | Cl | F | tetrahydrofuran-2-yl |
| 110 | Cl | Cl | tetrahydrofuran-2-yl |
| 111 | Br | F | tetrahydrofuran-2-yl |
| 112 | Br | Cl | tetrahydrofuran-2-yl |
| 113 | Cl | F | tetrahydrofuran-3-yl |
| 114 | Cl | Cl | tetrahydrofuran-3-yl |
| 115 | Br | F | tetrahydrofuran-3-yl |
| 116 | Br | Cl | tetrahydrofuran-3-yl |

The compounds of the formula II are novel and are useful intermediates in the preparation of benzoxazoles of the formula I. Accordingly, the compounds II likewise form part of the subject matter of the present invention.

Surprisingly, it has been found that the compounds II can be prepared starting from the 3-(pyrazol-3-yl)anilines of the formula III in good yields:

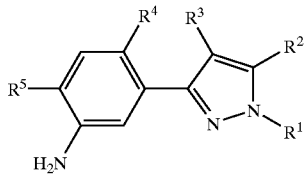

(III)

The process for preparing the compounds II from the compounds III comprises, according to a first variant, the following process steps:

i. halogenation of a 3-(pyrazol-3-yl)aniline of the formula III to give a 2-halo-3-(pyrazol-3-yl)aniline of the formula IV,

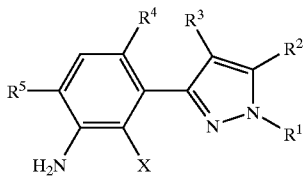

(IV)

ii. reaction of the 3-halo-2-(pyrazol-3-yl)aniline IV with an acylating agent of the formula $R^6$—C(O)—Y, in which Y is a leaving group, to give an anilide of the formula II and/or a diacyl compound of the formula V

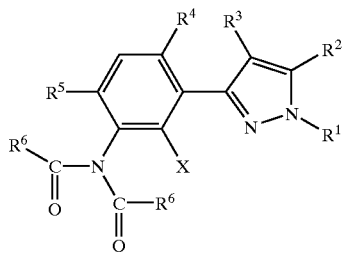

(V)

iii. if appropriate, partial solvolysis of the compound V to give the anilide of the formula II, where the variables $R^1$–$R^6$ and X in the compounds of the formulae III, IV and V are as defined above. With respect to the preferred and particularly preferred meanings of these variables, what was said above for the compounds II applies. This variant is used in particular when $R^3$ is different from hydrogen.

The 3-halo-2-(pyrazol-3-yl)anilines of the formula IV and the N,N-diacyl-3-halo-2-(pyrazol-3-yl)anilines of the formula V are likewise novel and are useful intermediates in the preparation of I from II. Moreover, the compounds II, IV and V surprisingly have good herbicidal activity which is furthermore superior to the herbicidal activity of prior-art compounds which, in place of the halogen atom X, contain a hydrogen atom. Accordingly, the compounds II, IV and V likewise form part of the subject matter of the present invention. For these compounds, what was said above for the variables $R^1$ to $R^6$ and X applies.

Accordingly, among the compounds of the formulae IV and V, particular preference is given to those compounds in which $R^1$ is methyl, $R^2$ is difluoromethoxy or trifluoromethyl and $R^5$ is chlorine (compounds IVa and Va ($R^2$=OCHF$_2$ and X=Br), compounds IVb and Vb ($R^2$=OCHF$_2$ and X=iodine), compounds IVc and Vc ($R^2$=CF$_3$ and X=Br), compounds IVd and Vd ($R^2$=CF$_3$ and X=iodine)).

Examples of preferred compounds of the formulae IVa to IVd are those in which $R^3$, $R^4$ and X each have the meaning given in one row of Table 2 (compounds IVa.1–IVa.8, IVb.1–IVb.8, IVc.1–IVc.8, IVd.1–IVd.8).

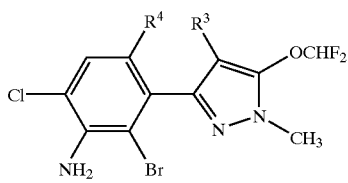

(IVa)

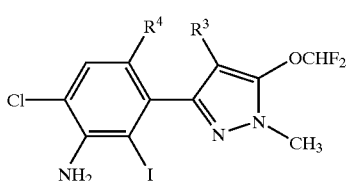

(IVb)

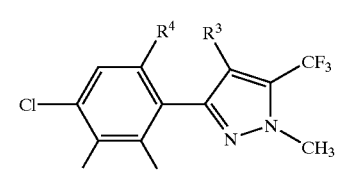

(IVc)

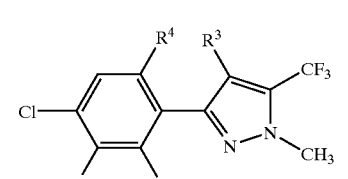

(IVd)

TABLE 2

| No. | $R^3$ | $R^4$ | X |
|---|---|---|---|
| 1 | Cl | F | Br |
| 2 | Cl | Cl | Br |
| 3 | Br | F | Br |
| 4 | Br | Cl | Br |
| 5 | Cl | F | I |
| 6 | Cl | Cl | I |
| 7 | Br | F | I |
| 8 | Br | Cl | I |

Particularly preferred compounds of the formula Va where $R^2$=OCHF$_2$ and X=Br are those compounds in which $R^3$, $R^4$ and $R^6$ have the meaning given in each case in one row of Table 1 (compounds Va.1–Va.116). Examples of preferred compounds of the formula Vb ($R^2$=OCHF$_2$ and X=iodine) are the compounds in which $R^3$, $R^4$ and $R^6$ in each case have the meaning given in one row of Table 1 (compounds Vb.1–Vb.116). Preferred compounds of the formula Vc where $R^2$=CF$_3$ and X=Br are those compounds in which $R^3$, $R^4$ and $R^6$ have the meaning given in each case in one row of Table 1 (compounds Vc.1–Vc.116). Examples of preferred compounds of the formula Vd ($R^2$=$CF_3$ and X=iodine) are the compounds in which $R^3$, $R^4$ and $R^6$ in each case have the meaning given in one row of Table 1 (compounds Vd.1–Vd.116).

Suitable halogenating agents for converting compounds of the formula III into the 2-halo-3-(pyrazol-3-yl)anilines of the formula IV (step i)) are bromine, mixtures of chlorine and bromine, bromine chloride, iodine, mixtures of iodine and chlorine, iodine chloride, N-halosuccinimides, such as N-bromosuccinimide and N-iodosuccinimide, hypohalic acids, such as hypobromic acid, and furthermore dibromoisocyanuric acid and the bromine/dioxane complex. The halogenating agent is generally employed in an equimolar amount or in excess, based on III, preferably in about the stoichiometrically required amount. The molar excess can be up to 5 times the amount of III. Among the abovementioned halogenating agents, preference is given to the brominating agents and the iodinating agents, and in a preferred embodiment of the invention, elemental bromine is used.

If appropriate, catalytic or stoichiometric amounts of a Lewis- or Brönsted-acidic catalyst, for example aluminum chloride or bromide, iron(III) chloride or bromide, or sulfuric acid, or a catalyst precursor from which the actual catalyst is formed during the reaction, for example iron, can be added to accelerate the reaction i). If the compound IV is to be prepared as iodide (X=iodine), it is also possible to add, as catalyst, nitric acid, iodic acid, sulfur trioxide, hydrogen peroxide or an aluminum chloride/copper(II) chloride complex.

In another variant of the reaction i), the desired halogen is employed in the form of a halide salt from which the halogen is released by adding an oxidizing agent. Examples of such "halogenating agents" are mixtures of sodium chloride or sodium bromide with hydrogen peroxide.

The halogenation is usually carried out in an inert solvent, for example a hydrocarbon, such as hexane, a halogenated hydrocarbon, such as dichloromethane, trichloromethane, 1,2-dichloroethane or chlorobenzene, in a cyclic ether, such as dioxane, in a carboxylic acid, such as acetic acid, propionic acid or butanoic acid, a mineral acid, such as hydrochloric acid or sulfuric acid, or in water. It is, of course, also possible to use mixtures of the abovementioned solvents.

If appropriate, the reaction is carried out in the presence of a base, for example an alkali metal hydroxide, such as KOH, or the alkali metal salt of a carboxylic acid, such as sodium acetate or sodium propionate.

In general, the reaction temperature is determined by the melting and the boiling point of the solvent in question. The reaction is preferably carried out at temperatures in the range from 0 to 100° C. and in particular in the range from 0 to 80° C.

In step ii), the 2-halo-3-(pyrazol-3-yl)aniline of the formula IV obtained in the reaction i) is reacted with an acylating agent $R^6$—C(O)—Y. Here, $R^6$ has the meanings mentioned above. Y is a customary leaving group.

Examples of acylating agents are carboxylic acids (Y=OH), carboxylic esters, such as $C_1$–$C_4$-alkyl esters (Y=$C_1$–$C_4$-alkyl, in particular methyl or ethyl), vinyl esters (Y=CH=$CH_2$), 2-propenyl esters (Y=C($CH_3$)=$CH_2$), acid anhydrides (Y=O—C(O)—$R^6$), acyl halides, in particular acyl chlorides (Y=halogen, in particular chlorine), mixtures of the anhydrides $R^6$—C(O)—O—C(O)—$R^6$ with carboxylic acids, such as formic acid, and also mixed anhydrides (Y=O—C(O)—R' where R'=H or, for example, $C_1$–$C_6$-alkyl), for example a mixed anhydride with pivalic acid (R'=tert-butyl) or with formic acid (compounds of the formula H—C(O)—O—C(O)—$R^6$).

The acylating agent is preferably employed in an amount of from 1.0 to 5 mol and in particular in an amount of from 1.0 to 2.0 mol, based on 1 mol of the compound IV.

If appropriate, catalytic or stoichiometric amounts of an acidic or basic catalyst are added during the acylation of IV. The catalyst is preferably employed in an amount of from 0.001 to 5 mol and in particular in an amount of from 0.01 to 1.2 mol, based on 1 mol of the compound IV.

Examples of basic catalysts are nitrogen bases, for example trialkyl amines, such as triethyl amine, pyridine compounds, such as pyridine itself or dimethylaminopyridine, furthermore oxo bases, such as sodium carbonate or potassium carbonate or the hydroxides of sodium, potassium or calcium.

Examples of acidic catalysts are, in particular, mineral acids, such as sulfuric acid.

The acylation is usually carried out in a solvent. Suitable solvents are, if appropriate, the liquid acylating agent itself or, if appropriate, the liquid catalyst. Suitable solvents are furthermore inert organic solvents, for example hydrocarbons, such as hexane or toluene, halogenated hydrocarbons, such as dichloromethane, trichloromethane, 1,2-dichloroethane or chlorobenzene, furthermore ethers, such as dioxane, tetrahydrofuran, methyl tert-butyl ether or dimethoxyethane.

In a preferred embodiment of this process step, the reaction of IV is carried out in a liquid anhydride in the presence of concentrated sulfuric acid. In another embodiment, the reaction is carried out in a two-phase system of water and a water-immiscible organic solvent. This embodiment is suitable in particular in the case where solid acylating agents, for example solid acyl chlorides, are used. In this case, the catalyst used is frequently a basic catalyst, in particular an inorganic base.

In a further preferred embodiment of this process step, the reaction of IV with an anhydride ($R^6$—CO)$_2$O or $R^6$—CO—O—CHO or a carboxylic acid $R^6$—COOH is carried out in the presence of concentrated sulfuric acid in an inert solvent. In general, this variant requires lower amounts of acylating agents, for example from 1 to 1.5 mol, per mole of compound IV. In this variant, the mono-N-acyl compounds II are surprisingly obtained in good yields and with high selectivity, without any significant amounts of the N,N-diacyl compounds V being formed.

In the acylation of IV, in addition to the anilide II, the diacyl compound of the formula V is also frequently formed. Depending on how the reaction is carried out, it can also be obtained as the only reaction product. In this case, the diacyl compound V, if appropriate in a mixture with the compound II, is subjected to partial solvolysis. Here, the compound V is cleaved into the compound II and a carboxylic acid $R^6$—COOH, its salt or a derivative, for example an ester $R^6$—COOR' (R', for example, =$C_1$–$C_4$-alkyl).

Suitable solvolyzing agents are, for example, water or alcohols, for example $C_1$–$C_4$-alkanols, such as methanol, ethanol or isopropanol, or mixtures of these alcohols with water.

The partial solvolysis of V is preferably carried out in the presence of an acidic or basic catalyst. Examples of basic catalysts are alkali metal hydroxides, such as sodium hydroxide or potassium hydroxide, or the alkoxides of $C_1$–$C_4$-alkanols, in particular sodium methoxide or potassium methoxide, or sodium ethoxide or potassium ethoxide. Examples of acidic catalysts are mineral acids, such as hydrochloric acid or sulfuric acid.

Usually, the solvolysis catalyst is employed in an amount of from 0.1 to 5 mol per mole of the compound V. In a preferred variant of this process step, the catalyst is employed in an amount of at least 0.5 mol/mole of compound V, and in particular in an about equimolar amount or in a molar excess, preferably of up to 2 mol, based on the compound V.

Preferred solvolysis agents are $C_1$–$C_4$-alkanols. Preferred catalysts are alkali metal hydroxides or alkali metal $C_1$–$C_4$-alkoxides, such as sodium hydroxides, sodium methoxide and sodium ethoxide.

Usually, the partial solvolysis is carried out in a solvent. Suitable solvents are, in particular, the solvolysis agents themselves, for example the $C_1$–$C_4$-alkanols, or mixtures of these solvolysis agents with inert solvents. Examples of inert solvents are the solvents mentioned above.

In a preferred embodiment of the present invention, the solvolysis of V to give II is carried out in a $C_1$–$C_4$-alkanol in the presence of the corresponding alkoxide, preferably methanol or ethanol using sodium methoxide and sodium ethoxide, respectively.

The solvolysis temperature is frequently above 0° C. and generally only limited by the boiling point of the solvent. Preferably, the reaction temperature is in the range from 0 to 100° C. and in particular in the range from 20 to 80° C.

The products IV, V and II obtained in steps i), ii) and iii) can be isolated by the work-up methods which are customary for this purpose. If appropriate, the reaction products of reaction ii) can be employed in the subsequent step iii) without further work-up. Frequently, the crude product of the compound II which is obtained in the reaction ii) or iii) is, prior to cyclization to the benzoxazole I, subjected to purification by crystallization and/or chromatography.

The 3-(pyrazol-3-yl)anilines of the formula III used as starting materials in the process according to the invention are known from the prior art, for example from WO 98/27090, WO 99/55702, WO 92/06962, WO 92/02509, WO 96/15115 or U.S. Pat. No. 5,032,165, or they can be prepared by methods similar to known processes. The compounds of the formula III for their part can be prepared by the processes described in WO 92/06962, WO 92/02509 or U.S. Pat. No. 5,032,165, starting from phenyl-substituted pyrazoles of the formula VI

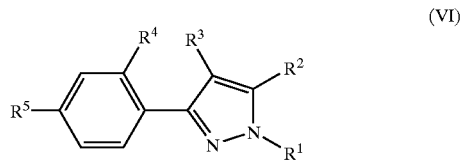

(VI)

by successive nitration and hydrogenation of the nitro group formed.

The nitration of the 3-(pyrazol-3-yl)benzenes VI gives, in a smooth reaction, the corresponding 3-(pyrazol-3-yl)-1-nitro-benzenes of the formula VII,

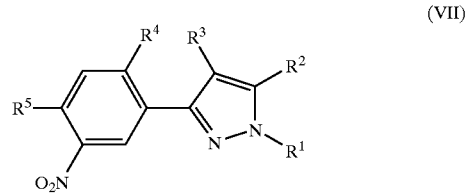

(VII)

in which $R^1$–$R^5$ are as defined above. Surprisingly, this reaction takes place without the pyrazole ring of VI being nitrated to any significant extent, even if $R^3$ is hydrogen. Compounds of the formula VI in which $R^3$ is hydrogen are hereinbelow also referred to as compounds VI-A. This applies correspondingly to the compounds VII.

The nitration of VI can be carried out with customary nitrating agents as described in the prior art for the nitration of aromatic compounds and also in WO 92/06962, WO 92/02509 or U.S. Pat. No. 5,032,165. Suitable reagents are nitric acid of different concentrations, including concentrated and fuming nitric acid, mixtures of concentrated sulfuric acid and nitric acid (nitrating acid), and furthermore acyl nitrates and alkyl nitrates.

The nitration can be carried out in the absence of a solvent, in excess nitrating agent or in an inert solvent or diluent, suitable inert solvents or diluents being, for example, water, mineral acids, organic acids, halogenated hydrocarbons, such as methylene chloride, anhydrides, such as acetic anhydride, and mixtures of these solvents.

Depending on the reagent, starting material VI or VI-A and nitrating agent can be employed in approximately equimolar amounts. However, to optimize the conversion of starting material, it may be advantageous to use an excess of nitrating agent, for example up to about 20 times the molar amount, based on VI. If the reaction is carried out in the absence of a solvent in the nitrating agent, for example in nitrating acid, the nitrating agent is present in an even greater excess.

The reaction temperature is usually from –100° C. to 200° C., preferably from –30 to 50° C.

The preferred nitrating agent is nitrating acid, i.e. a mixture of concentrated sulfuric acid and concentrated, preferably 100% strength, nitric acid. For the nitration, the compound VI or VI-A is preferably dissolved or suspended in sulfuric acid, and the nitric acid is then added, preferably under temperatures control. The reaction is then preferably carried out at temperatures in the range from –30 to 50° C., preferably in the range from –20 to +30° C. The duration of the reaction is generally from 0.5 to 5 h.

The nitrated compound VII or VII-A (=compound VII where $R^3$=H) is isolated from the reaction mixture in a customary manner, for example by pouring the reaction mixture into water and/or onto ice, followed by filtration or extraction of the resulting reaction product. If appropriate, the aqueous phase is neutralized prior to the isolation of the reaction mixture using a neutralizing agent, for example alkali metal hydroxides, carbonates or bicarbonates. If required, the reaction product can then be recrystallized.

The reduction of the resulting nitro compounds VII or VII-A to the 3-(pyrazol-3-yl)anilines of the formula III is carried out using customary reducing agents for aromatic nitro groups as described in the prior art for reducing aromatic nitro compounds to the corresponding anilines (see, for example, J. March, Advanced Organic Chemistry, $3^{rd}$ ed., J. Wiley & Sons, New York, 1985, p. 1183 and literature cited therein), and also in EP-A 361114, WO 92/06962, WO 92/02509 or U.S. Pat. No. 5,032,165, which are expressly incorporated herein by way of reference.

The reduction is carried out, for example, by reacting the nitro compound VII with a metal such as iron, zinc or tin under acidic reaction conditions, i.e. with nascent hydrogen, or with a complex hydride, such as lithium aluminum hydride or sodium borohydride, preferably in the presence of transition metal compounds of nickel or cobalt, such as $NiCl_2(P(phenyl)_3)_2$, or $CoCl_2$, (see Ono et al., Chem. Ind. (London), 1983, p. 480) or with $NaBH_2S_3$ (see Lalancette et al., Can. J. Chem. 49, (1971), p. 2990), where, depending on the reagent used, these reductions can be carried out neat or in a solvent or diluent. Suitable solvents are, depending on the reducing agent, for example alcohols, such as methanol, ethanol, n- and isopropanol, n-, 2-, iso- and tert-butanol, furthermore hydrocarbons, such as hexane or toluene, halogenated hydrocarbons, such as dichloromethane, trichloromethane, 1,2-dichloroethane or chlorobenzene, furthermore ethers, such as dioxane, tetrahydrofuran, methyl tert-butyl ether or dimethoxyethane, and also aliphatic carboxylic acids and their esters, for example acetic acid or propionic acid, with the abovementioned $C_1$–$C_4$-alcohols, or mixtures of the abovementioned solvents.

In the case of the reduction with a metal, the reaction is preferably carried out in the absence of a solvent in an inorganic acid, in particular in concentrated or dilute hydrochloric acid, or in a liquid organic acid, such as acetic acid or propionic acid. However, the acid can also be diluted with an inert solvent, for example one of those mentioned above. The reduction with complex hydrides is preferably carried out in a solvent, for example an ether or an alcohol.

Frequently, the reduction of VII to III is carried out using hydrogen in the presence of a transition metal catalyst, for example hydrogen in the presence of catalysts based on platinum, palladium, nickel, ruthenium or rhodium. The catalysts can contain the transition metal in elemental form or in the form of a complex compound, a salt or an oxide of the transition metal, where customary coligands, for example organic phosphine compounds, such as triphenylphosphine, tricyclohexylphosphine, tri-n-butylphosphine or phosphites, can be used for modifying the activity. The catalyst is usually employed in amounts of from 0.001 to 1 mol per mole of the compound VII, calculated as catalyst metal.

The catalyst can be employed in supported or unsupported form. Suitable supports are, for example, activated carbon, calcium carbonate, calcium sulfate, barium sulfate, silica gel, alumina, alumosilicates, zeolites or organic polymers, for example popcorn polymers based on N-vinyllactams or polystyrenes having functional groups suitable for binding the catalyst metal. A suitable catalyst is in particular also finely divided nickel, for example in the form of Raney nickel.

The conversion of VII into III is frequently carried out with hydrogen in the presence of a transition metal catalyst in an inert organic solvent. Suitable solvents are, in principle, all of the abovementioned solvents. Preferred solvents are the abovementioned alcohols and their mixtures with ethers or esters, in particular if the catalyst used is finely divided nickel.

The hydrogen pressure required for the reduction can be varied within a wide range and is generally in the range from atmospheric pressure up to a superatmospheric pressure of 50, preferably up to 10, and in particular up to 3, bar. Of course, the reaction can also be carried out at hydrogen partial pressures below atmospheric pressure, for example in the range from 0.2 to 1 bar.

The temperature required for the reaction can be varied within a wide range and is, depending on the reactivity of the catalyst and the chosen hydrogen partial pressure, usually in the range from 0 to 150° C., preferably in the range from 10 to 100° C., it being possible to carry out the reaction both at lower temperatures and at higher temperatures.

In a particular embodiment of the process according to the invention for preparing the compounds III in which X and $R^3$ are bromine or iodine, the 3-(pyrazol-3-yl)benzenes of the formula VI-A are used directly as starting materials.

In a first step a), these compounds are reacted with a nitrating agent to give a 3-(pyrazol-3-yl)-1-nitrobenzene VII-A

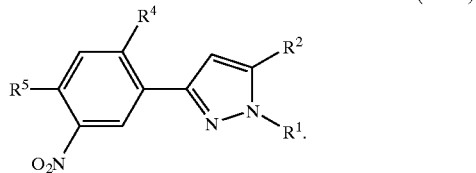

(VII-A)

The compound VII-A is then, in a step b), reacted with a reducing agent to give a 3-(pyrazol-3-yl)aniline of the formula III-A (compound III where $R^3$=H). The compounds III-A can then be brominated directly, in the manner described above, to give the compounds IV in which both $R^3$ and X are bromine (compounds IV-$Br_2$), or they can be iodinated to compounds IV-$I_2$ in which both $R^3$ and X are iodine.

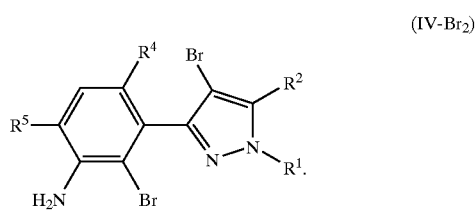

(IV-$Br_2$)

Steps ii and, if appropriate, iii are then carried out in the manner described above.

The halogenation of III-A to IV is carried out in the manner described above, similarly to the halogenation of III to IV. To achieve complete conversion, differing from the halogenation of III to IV, the halogenating agent is preferably employed in an amount of at least about 2 equivalents, based on III-A, for example in a molar ratio of from 1:1.9 to 1:2.5, it also being possible to use an even greater excess of halogenating agent. For the conversion of III-A into IV-$Br_2$ or IV-$I_2$, the preferred halogenating agent is elemental halogen, preferably bromine. The reaction is then preferably carried out in a carboxylic acid, such as acetic acid, propionic acid or butanoic acid, or in a mineral acid, such as hydrochloric acid or sulfuric acid, in mixtures of these acids, in water, or in a mixture of at least one of these acids with water. The temperatures required for the reaction can be determined by the person skilled in the art in simple routine experiments, and they are preferably in the range from –10° C. to 120° C. and in particular in the range from 10° C. to 60° C.

The compounds of the formulae II, IV and V and their agriculturally useful salts are surprisingly—both as isomer mixtures and in the form of the pure isomers—suitable for use as herbicides.

Suitable agriculturally useful salts are especially the salts of those cations or the acid addition salts of those acids whose cations and anions, respectively, do not have any adverse effect on the herbicidal action of the compounds II, IV and V. Thus, suitable cations are in particular the ions of the alkali metals, preferably sodium and potassium, of the alkaline earth metals, preferably calcium, magnesium and barium, and of the transition metals, preferably manganese, copper, zinc and iron, and also the ammonium ion which, if desired, may carry 1 to 4 $C_1$–$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri ($C_1$–$C_4$-alkyl)sulfonium, and sulfoxonium ions, preferably tri($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and also the anions of $C_1$–$C_4$-alkanoic acids, preferably formate, acetate, propionate and butyrate. They can be formed by reacting I with an acid of the corresponding anion, preferably of hydrochloric acid, hydrobromic acid, sulfuric acid, phosphoric acid or nitric acid.

With respect to the herbicidal activity of the compounds II, IV and V, the variables X and $R^1$ to $R^6$, alone or in combination, are preferably as defined below:

$R^1$ is hydrogen or $C_1$–$C_4$-alkyl, in particular methyl or ethyl;

$R^2$ is cyano, difluoromethoxy, trifluoromethyl or methylsulfonyl;

$R^3$ is halogen;

$R^4$ is halogen;

$R^5$ is fluorine, chlorine or cyano;

X is bromine;

$R^6$ is hydrogen, $C_1$–$C_4$-alkyl, $C_1$–$C_4$-haloalkyl, $C_2$–$C_4$-alkenyl, $C_2$–$C_4$-haloalkenyl, $C_2$–$C_4$-alkynyl, $C_1$–$C_4$-alkoxy-$C_1$–$C_4$-alkyl, $C_1$–$C_4$-alkoxycarbonyl-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl, 4- to 7-membered heterocyclyl or heterocyclyl-$C_1$–$C_4$-alkyl, where the phenyl ring, the cycloalkyl ring and the heterocyclyl ring can be unsubstituted or may carry one or two substituents, selected from the group consisting of cyano, halogen, $C_1$–$C_4$-alkyl, $C_1$–$C_4$-haloalkyl and $C_1$–$C_4$-alkoxy. Examples of preferred meanings of $R^6$ are given in Table 1.

Among these, particular preference is given to the compounds II, IV and V in which $R^1$ is methyl. $R^2$ is in particular trifluoromethyl and particularly preferably difluoromethoxy. $R^3$ is in particular chlorine or bromine. $R^4$ is in particular fluorine or chlorine. $R^5$ is in particular chlorine. $R^6$ is in particular hydrogen, $C_1$–$C_4$-alkyl, $C_1$–$C_4$-alkoxy-$C_1$–$C_4$-alkyl, $C_3$–$C_8$-cycloalkyl, $C_3$–$C_8$-cycloalkyl-$C_1$–$C_4$-alkyl, phenyl or phenyl-$C_1$–$C_4$-alkyl. X is in particular bromine.

Herbicidal compositions comprising the compounds II, IV or V or mixtures of these compounds and/or their agriculturally compatible salts control vegetation on non-crop areas very efficiently, especially at high application rates. They act against broad-leaved weeds and grass weeds in crops such as wheat, rice, corn, soya and cotton without causing any significant damage to the crop plants. This effect is mainly observed at low application rates.

Depending on the application method in question, the compounds II, IV or V, or mixtures of these compounds, or their agriculturally compatible salts, or compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N. rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (s. *vulgare*), *Theobroma cacao, Trifolium pratense, Triticum aestivum, Triticum durum, Vicia faba, Vitis vinifera* and *Zea mays.*

In addition, the compounds II, IV or V may also be used in crops which tolerate the action of herbicides owing to breeding, including genetic engineering methods.

Moreover, the compounds II, IV and V and their agriculturally useful salts are also suitable for the desiccation and/or defoliation of plants.

As desiccants, they are suitable, in particular, for desiccating the aerial parts of crop plants such as potatoes, oilseed rape, sunflowers and soybeans. This allows completely mechanical harvesting of these important crop plants.

Also of economic interest is;

concentrating into a short period of time fruit drop or reducing their adherence to the plant, in citrus fruits, olives or other species and varieties of pomaceous fruit, stone fruit and nuts, as this facilitates harvesting of these fruits, and also the controlled defoliation of useful plants, in particular cotton.

The drop, which is promoted by the use of compounds of formula II, IV and/or V according to the invention and their agriculturally useful salts, is due to the formation of abscission tissue between fruit or leaf and shoot of the plants. Defoliation of cotton is of particular economic interest, since this facilitates harvesting. At the same time shortening the period within which the individual plants mature results in improved fiber quality after harvesting.

The compounds II, IV and V, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting, or granules, by means of spraying, atomizing, dusting, spreading, watering or treating the seed or mixing with the seed. The use forms depend on the intended purpose; in any case, they should ensure the finest possible distribution of the active ingredients according to the invention. The herbicidal compositions comprise a herbicidally effective amount of at least one compound of the formula II, IV or V or an agriculturally useful salt of II, IV or V and auxiliaries customarily used for formulating crop protection agents.

Suitable as inert auxiliaries are essentially the following:
mineral oil fractions of medium to high boiling point, such as kerosene and diesel oil, furthermore coal tar oils and oils of vegetable or animal origin, aliphatic, cyclic and aromatic hydrocarbons, e.g. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the compounds of the formula II, IV or V, either as such or dissolved in an oil or solvent, can be homogenized in water by means of a wetting agent, tackifier, dispersant or emulsifier. Alternatively, it is possible to prepare concentrates comprising active ingredient, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or grinding the active ingredients together with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

The concentrations of the active ingredients II, IV and V in the ready-to-use preparations can be varied within wide ranges. In general, the formulations comprise from 0.001 to 98% by weight, preferably 0.01 to 95% by weight of at least one active compound. The active compounds are employed in a purity of from 90% to 100%, preferably 95% to 100% (according to NMR spectrum).

The compounds II, IV or V according to the invention can be formulated for example as follows:

I 20 parts by weight of the compound No. IIa.9 (see Table 1) are dissolved in a mixture composed of 80 parts by weight of alkylated benzene, 10 parts by weight of the adduct of from 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II 20 parts by weight of the compound No. IIa.17 (see Table 1) are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III 20 parts by weight of the active ingredient No. IIa.12 (see Table 1) are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV 20 parts by weight of the active ingredient No. IIa.69 (see Table 1) are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V 3 parts by weight of the active ingredient No. IVa.1 (see Table 2) are mixed with 97 parts by weight of finely divided kaolin. This gives a dust which comprises 3% by weight of the active ingredient.

VI 20 parts by weight of the active ingredient No. IVa.4 (see Table 2) are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII 1 part by weight of the compound No. Va.9 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of the compound No. Va.12 is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The herbicidal compositions or the active ingredients can be applied pre- or post-emergence or together with the seed of a crop plant. It is also possible to apply the herbicidal compositions or active ingredients by broadcasting crop plant seed pre-treated with the herbicidal compositions or active ingredients. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

The rates of application of active ingredient II, IV or V are from 0.001 to 3.0, preferably 0.01 to 1.0, kg/ha of active substance (a.s.), depending on the control target, the season, the target plants and the growth stage.

To widen the spectrum of action and to achieve synergistic effects, the compounds II, IV or V may be mixed with a large number of representatives of other herbicidal or growth-regulating active ingredients and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acid and its derivatives, benzoic acid and its derivatives, benzothiadiazinones, 2-aroyl-1,3-cyclohexanediones, 2-hetaroyl-1,3-cyclohexanediones, hetaryl aryl ketones, benzylisoxazolidinones, meta-$CF_3$-phenyl derivatives, carbamates, quinolinic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds II, IV and/or V, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

The examples below serve to illustrate the invention, but without limiting it.

All $^1$H-NMR spectra were measured in $CDCl_3$ in a 270 MHz spectrometer. The chemical shift with respect to TMS in ppm and the integral of the signal in question were determined. The following abbreviations were used: s=singlet, d=doublet, q=quartet, t=triplet, br=broad signal.

EXAMPLE 1

Preparation of 2-ethyl-4,6-dichloro-7-(4-bromo-5-difluoromethoxy-1-methyl-1H-pyrazol-3-yl)benzoxazole (1)

1.1 2-bromo-4,6-dichloro-3-(4-bromo-5-difluoromethoxy-1-methyl-1H-pyrazol-3-yl)aniline IVa.4

Variant A 50 g (0.12 mol) of 4,6-dichloro-3-(4-bromo-5-difluoromethoxy-1-methyl-1H-pyrazol-3-yl)aniline were dissolved in 200 ml of dichloromethane and mixed with 20 g (0.13 mol) of bromine. The reaction mixture was stirred at room temperature until no further changes were found by HPLC ($C_{18}$ column, methanol/water gradient 0–100). The reaction mixture was then extracted with saturated sodium bicarbonate solution and saturated sodium chloride solution. The organic phase was dried over magnesium sulfate and concentrated. Chromatography of the residue over silica gel (ethyl acetate/cyclohexane) gave 60 g of 2-bromo-4,6-dichloro-3-(4-bromo-5-difluoromethoxy-1-methyl-1H-pyrazol-3-yl)aniline IVa.4.

$^1$H-NMR δ ppm: 7.4 (s, 1H), 6.7 (t, 1H), 4.2 (br, 2H) 3.9 (S, 3H)

Variant B 50 g (0.129 mol) of 4,6-dichloro-3-(4-bromo-5-difluoromethoxy-1-methyl-1H-pyrazol-3-yl)aniline were added to 150 ml of glacial acetic acid. The mixture was admixed with 53 g (0.64 mol) of sodium acetate. At room temperature, 20.6 g (0.129 mol) of bromine were added dropwise, and the mixture was stirred overnight. The acetic acid was removed under reduced pressure, the residue was admixed with 50 ml of toluene and the mixture was concentrated to dryness. The residue was taken up in 200 ml of ethyl acetate, washed with 100 ml of 2 N NaOH solution, dried over magnesium sulfate and concentrated. This gave 56 g of the title compound.

1.2 N-propionyl-2-bromo-4,6-dichloro-3-(4-bromo-5-difluoromethoxy-1-methyl-1H-pyrazol-3-yl)anilide IIa.12

Variant A 48 g (0.103 mol) of the compound IVa.4 were dissolved in 480 ml of propionic anhydride, and 0.5 g of concentrated sulfuric acid were added to this solution. The solution was then stirred at 75° C. for 1 h. The reaction mixture was concentrated under reduced pressure and diluted with methyl tert-butyl ether and water, and the organic phase was separated off. The organic phase was then washed with saturated sodium bicarbonate solution and dried over magnesium sulfate. Concentration of the solvent to dryness gave 57.4 g of the dipropionyl compound (compound V where $R^1$=methyl, $R^2$=difluoromethoxy, $R^3$=bromine, $R^4$=$R^5$=chlorine, X=bromine and $R^6$=ethyl), which contained minor amounts of the corresponding N-propionylanilide IIa.12. The resulting mixture was then subjected to partial solvolysis. To this end, the reaction product of the acylation was dissolved in 300 ml of methanol, and 17.9 g of a 30% by weight strength solution of sodium methoxide and methanol was added to the solution. The mixture was then stirred at room temperature until no further conversion was observed with HPLC ($C_{18}$ column, methanol/water gradient 0–100). For work-up, about 500 ml of dichloromethane were added to the reaction mixture, and the resulting solution was washed successively with dilute hydrochloric acid, water and saturated aqueous sodium chloride solution. Chromatography over silica gel (mobile phase: cylohexane/ethyl acetate) gave 41.4 g of N-propionyl-2-bromo-4,6-dichloro-3-(4-bromo-5-difluoromethoxy-1-methyl-1H-pyrazol-3-yl) anilide IIa.12. Melting point: 173–175° C.

$^1$H-NMR δ ppm: 7.6 (s, 1H), 7.2 (br. s, 1H), 6.7 (t, 1H), 3.9 (s, 3H), 2.5 (br. q, 2H), 1.3 (br. t, 3H).

In the $^1$H-NMR spectrum, the dipropionyl compound showed the following signals:

$^1$H-NMR δ ppm: 7.7 (s, 1H), 6.7 (t, 1H), 3.9 (s, 3H), 2.8–2.4 (m, 4H), 1.2 (m, 6H).

Variant B 56 g (0.12 mol) of aniline IVa.4 from the previous step were dissolved in 500 ml of toluene and admixed with 0.6 g of concentrated sulfuric acid and 17.2 g (0.13 mol) of propionic anhydride. The mixture was stirred at room temperature for 2 h, and the precipitate was filtered off with suction, washed with a little methyl tert-butyl ether, taken up in 300 ml of ethyl acetate and admixed with just enough 10% NaOH solution for dissolving the product completely. The organic phase was separated off and 49 g of the title compound IIa.12 were isolated from this phase by concentration.

1.3 2-ethyl-4,6-dichloro-7-(4-bromo-5-difluoromethoxy-1-methyl-1H-pyrazol-3-yl)benzoxazole (1)

a) Variant Using an Equimolar Amount of CuBr

At 70° C., 2 g of the anilide IIa.12 (0.0038 mol) were reacted with 0.1 g (0.0038 mol) of sodium hydride (97% by weight) in 20 ml of DMSO, until the evolution of gas had ceased. 0.55 g (0.0038 mol) of copper(I) bromide was then added and the mixture was heated at 140° C. until HPLC showed no further changes. The mixture was cooled to room temperature, ice-water was added and the mixture was extracted with about 100 ml of ethyl acetate. The extract was dried over sodium sulfate, the solvent was evaporated to dryness and the residue was chromatographed over silica gel (mobile phase: cyclohexane/ethyl acetate). This gave 1.1 g of the benzoxazole (1).

Melting point: 131–132° C.

$^1$H-NMR δ ppm: 7.5 (s, 1H), 6.7 (t, 1H), 3.9 (s, 3H), 2.4 (q, 2H), 1.4 (t, 3H)

b) Variant with a Catalytic Amount of CuCl 3 g (5.7 mmol) of anilide IIa.12 were dissolved in 10 ml of dimethylformamide and 1 ml of pyridine. 0.43 g (3.1 mmol) of $K_2CO_3$ were added, and the mixture was heated at 90° C. for 2 h. 0.12 g (1.2 mmol) of Cu(I)Cl were then added, and the mixture was stirred at 140° C. for 2 h. The reaction mixture was concentrated under reduced pressure and the residue was chromatographed on silica gel using cyclohexane/ethyl acetate 9/1. This gave 1.9 g of the benzoxazole (1).

c) Variant with a Catalytic Amount of CuBr

Similarly to the previous variant, 3 g of the anilide IIa.12 were reacted with 0.3 g (2.3 mmol) of Cu(I)Br and 0.43 g (3.1 mmol) of $K_2CO_3$ under otherwise identical conditions. This gave 1.96 g of the benzoxazole (1).

d) Variant with a Catalytic Amount of Cu(I)I:

Similarly to the previous variant, 3 g of the anilide IIa.12 were reacted with 0.23 g (1.2 mmol) of Cu(I)I and 0.43 g (3.1 mmol) of $K_2CO_3$ under otherwise identical conditions. This gave 1.8 g of the benzoxazole (1).

e) Variant with a Catalytic Amount of Cu(I)Br and the Base $KHCO_3$:

Similarly to the previous variant, 3 g of the anilide IIa.12 were reacted with 0.63 g (6.3 mmol) of $KHCO_3$ and 0.17 g (1.2 mmol) of Cu(I)Br under otherwise identical conditions. This gave 1.8 g of the benzoxazole (1).

EXAMPLE 2

Preparation of 2-ethyl-4-chloro-6-fluoro-7-(4-chloro-2-difluoromethoxy-1-methyl-1H-pyrazol-3-yl)benzoxazole (2)

2.1 2-bromo-4-fluoro-6-chloro-3-(4-chloro-5-difluoromethoxy-1-methyl-1H-pyrazol-3-yl)aniline IVa.1

Variant A 57 g (0.165 mol) of 4-fluoro-6-chloro-3-(4-chloro-5-difluoromethoxy-1-methyl-1H-pyrazol-3-yl)aniline were dissolved in 300 ml of dichloromethane and admixed with 26.5 g (0.165 mol) of bromine. The reaction mixture was stirred at room temperature until HPLC (see above) showed no further changes. The reaction mixture was concentrated. This gave 61 g of the compound IVa.1.

$^1$H-NMR δ ppm: 7.2 (s, 1H), 6.7 (t, 1H), 4.5 (br, 2H) 3.9 (S, 3H)

Variant B 19.5 g (59 mmol) of 6-chloro-4-fluoro-3-(4-chloro-5-difluoro-methoxy-1-methyl-1H-pyrazol-3-yl)aniline were added to 200 ml of glacial acetic acid. 47.8 g (0.59 mol) of sodium acetate were added to this mixture. At room temperature, 10.3 g (64 mmol) of bromine were added dropwise, and the mixture was stirred overnight. The acetic acid was removed under reduced pressure and the residue was admixed with 200 ml of toluene and concentrated to dryness. The residue was taken up in 200 ml of dichloromethane, washed with 200 ml of 5% strength aqueous NaOH solution, dried over magnesium sulfate and concentrated. This gave 24 g of the title compound IVa.1.

2.2 N-propionyl-2-bromo-4-fluoro-6-chloro-3-(4-chloro-5-difluoro-methoxy-1-methyl-1H-pyrazol-3-yl)anilide IIa.9

Variant A 43 g (0.106 mol) of the compound IVa.1 were dissolved in 200 ml of propionic anhydride, and 0.5 g of concentrated sulfuric acid was added. The mixture was then stirred at 75° C. for 1 h. The reaction mixture was concentrated under reduced pressure and diluted with methyl tert-butyl ether and water, and the organic phase was separated off. The organic phase was then washed with saturated aqueous sodium bicarbonate solution and dried over magnesium sulfate. Evaporation of the solvent to dryness gave 47 g of the dipropionyl compound (compound V where $R^1$=methyl, $R^2$=difluoromethoxy, $R^3$=chlorine, $R^4$=fluorine, $R^5$=chlorine, X=bromine and $R^6$=ethyl) which contained minor amounts of the corresponding N-propionylanilide IIa.9. The resulting mixture was then subjected to partial solvolysis. To this end, the reaction product of the acylation was dissolved in 100 ml of methanol, and 32.7 g of a 30% strength by weight solution of sodium methoxide in methanol was added to the solution. The mixture was then stirred at room temperature until HPLC (see above) showed no further conversion. For work-up, about 500 ml of dichloromethane were added to the reaction mixture, and the resulting solution was washed successively with dilute hydrochloric acid, water and saturated aqueous sodium chloride solution. Chromatography over silica gel (mobile phase: cyclohexane/ethyl acetate) gave 14 g of N-propionyl-2-bromo-4-fluoro-6-chloro-3-(4-chloro-5-difluoro-methoxy-1-methyl-1H-pyrazol-3-yl)anilide IIa.13.

$^1$H-NMR δ ppm: 7.6 (br. s, 1H), 7.3 (d, 1H), 6.7 (t, 1H), 3.9 (s, 3H), 2.4 (q, 2H), 1.3 (t, 3H)

Variant B 23 g (57 mmol) of aniline IVa.1 were dissolved in 20 ml of toluene and admixed with 0.28 g of concentrated sulfuric acid and 8.1 g (63 mmol) of propionic anhydride. The mixture was stirred at room temperature for 16 h and then diluted with 100 ml of water and 100 ml of toluene, the phases were separated and the aqueous phase was extracted once more with a total of 200 ml of toluene. The combined organic phases were dried over magnesium sulfate and then concentrated. The residue was taken up in 50 ml of cyclohexane/ethyl acetate 4:1 (v/v), heated and then filtered off with suction. This gave 21 g of the title compound IIa.13.

2.3 2-ethyl-4-chloro-6-fluoro-7-(4-chloro-5-difluoromethoxy-1-methyl-1H-pyrazol-3-yl)benzoxazole (2)

At 70° C., 14 g (0.03 mol) of the compound IIa.9 were reacted with 0.75 g (0.03 mol) of sodium hydride (as a 97% by weight suspension in mineral oil) in 50 ml of DMSO until the evolution of gas had ceased. 0.56 g (0.0039 mol) of copper(I) bromide were then added and the mixture was heated at 140° C., until HPLC showed no further changes. The mixture was cooled to room temperature, ice-water was added and the mixture was extracted with about 100 ml of ethyl acetate. The extract was dried over magnesium sulfate, the solvent was then evaporated to dryness and the residue was chromatographed over silica gel (mobile phase: cyclohexane/ethyl acetate). This gave 1.1 g of the benzoxazole (6).

Melting point: 73–75° C.

$^1$H-NMR δ ppm: 7.3 (s, 1H), 6.7 (t, 1H), 3.9 (s, 3H), 3.0 (q, 2H), 1.44 (t, 3H)

EXAMPLE 3
Preparation of 2-methyl-4,6-dichloro-7-(4-bromo-2-difluoromethoxy-1-methyl-1H-pyrazol-3-yl)benzoxazole (3)

3.1 N-Acetyl-2-bromo-4,6-dichloro-3-(4-bromo-5-difluoromethoxy-1-methyl-1H-pyrazol-3-yl)anilide IIa.8

Similarly to example 1.2 variant A, 5.0 g (0.011 mol) of the aniline IVa.4 were initially reacted in 100 ml of glacial acetic acid under otherwise identical conditions, and the diacetyl compound Va.8 initially obtained was then cleaved using 8.5 g (0.047 mol) of sodium methoxide in methanol. This gave 5.26 g of the anilide IIa.8.

$^1$H-NMR (CDCl$_3$) δ (ppm) 7.6 (s, 1H), 7.1 (br. s, 1H), 6.7 (t, 1H), 3.9 (s, 3H), 2.1 (s, 3H).

3.2 2-Methyl-4,6-dichloro-7-(4-bromo-5-difluoromethoxy-1-methyl-1H-pyrazol-3-yl)benzoxazole (3)

5.2 g (0.01 mol) of anilide IIa.8 in 100 ml of dimethyl sulfoxide were reacted with 0.24 g (0.01 mol of NaH and 0.22 g (1.5 mmol) of Cu(I)Br according to the procedure of example 2.1. This gave 1.9 g of the benzoxazole (3).

$^1$H-NMR (CDCl$_3$) δ (ppm) 7.5 (s, 1H), 6.8 (t, 1H), 3.9 (s, 3H), 2.6 (s, 3H).

EXAMPLE 4
2-tert-Butyl-4,6-dichloro-7-(4-bromo-5-difluoromethoxy-1-methyl-1H-pyrazol-3-yl)benzoxazole (4)

4.1 N-Pivaloyl-2-bromo-4,6-dichloro-3-(4-bromo-5-difluoromethoxy-1-methyl-1H-pyrazol-3-yl)anilide IIa.36

3.8 g (8.2 mmol) of aniline IVa.4, dissolved in 100 ml of dichloromethane, were admixed with 3.9 g (49.2 mmol) of pyridine and a catalytic amount of 4-dimethylaminopyridine. 3.2 g (24.7 mmol) of pivaloyl chloride were added dropwise to this mixture.

The resulting mixture was heated at 40° C. and stirred until thin-layer chromatography (cyclohexane/ethyl acetate 4/1 v/v) showed no further changes. The mixture was diluted with 200 ml of ethyl acetate and washed twice with 200 ml of 10% strength hydrochloric acid and once with 100 ml of saturated NaHCO$_3$ solution, and the organic phase was dried over magnesium sulfate. Silica gel chromatography (cyclohexane/ethyl acetate 4/1 v/v) of the residue obtained after concentration gave 1.4 g of the anilide IIa.36.

$^1$H-NMR (CDCl$_3$) δ (ppm) 7.6 (s, 1H), 7.2 (br, 1H), 6.7 (t, 1H) 3.8 (s, 3H), 1.4 (s, 9H).

4.2 2-tert-Butyl-4,6-dichloro-7-(4-bromo-5-difluoromethoxy-1-methyl-1H-pyrazol-3-yl)benzoxazole (4)

1.3 g (2.4 mmol) of anilide IIa.36 were dissolved in 10 ml of dimethylformamide and 1 ml of pyridine and admixed with 0.26 g (2.6 mmol) of KHCO$_3$. The mixture was heated at 90° C. for 1.5 h. 0.07 g (0.5 mmol) of Cu(I)Br was then added, and the mixture was stirred at 140° C. for 2 h. The reaction mixture was concentrated and the residue was chromatographed on silica gel (cyclohexane/ethyl acetate 4/1 v/v), giving 0.34 g of benzoxazole (4).

$^1$H-NMR (CDCl$_3$) δ (ppm) 7.5 (s, 1H), 6.8 (t, 3H), 3.9 (s, 3H), 1.5 (s, 9H).

EXAMPLE 5
2-Methyl-4-chloro-6-fluoro-7-(4-chloro-5-difluoromethoxy-1-methyl-1H-pyrazol-3-yl)benzoxazole (5)

5.1 N-Acetyl-2-bromo-4-fluoro-6-chloro-3-(4-chloro-5-difluoro-methoxy-1-methyl-1H-pyrazol-3-yl)anilide IIa.5

Similarly to the preparation procedure of example 2.2, 13.5 g (33 mmol) of the aniline IVa.1 from example 2.1 were reacted in 100 ml of glacial acetic acid under otherwise identical reaction conditions. The diacetyl compound Va.5 initially obtained was cleaved using 9.6 g (53 mmol) of sodium methoxide in methanol, giving 7.7 g of the anilide IIa.5.

$^1$H-NMR (CDCl$_3$) δ (ppm) 7.3 (d, 1H), 6.9 (br. s, 1H), 6.7 (t, 1H), 3.9 (s, 3H), 2.2 (s, 3H).

5.2 2-Methyl-4-chloro-6-fluoro-7-(4-chloro-5-difluoromethoxy-1-methyl-1H-pyrazol-3-yl)benzoxazole (5)

Reaction of 7.7 g (17.2 mmol) of amide IIa.5 by the procedure described in 2.3 gave 4.28 g of the benzoxazole (5).

$^1$H-NMR (CDCl$_3$) δ (ppm) 7.2 (d, 1H), 6.8 (t, 1H), 3.9 (s, 3H), 2.7 (s, 3H).

EXAMPLE 6
Preparation of 2-methoxymethyl-4-chloro-6-fluoro-7-(4-chloro-5-difluoromethoxy-1-methyl-1H-pyrazol-3-yl)-benzoxazole (6)

6.1 N-Methoxyacetyl-2-bromo-4-fluoro-6-chloro-3-(4-chloro-5-difluoromethoxy-1-methyl-1H-pyrazol-3-yl) aniline IIa.69

5.63 g (14 mmol) of the aniline compound IVa.1 from example 2.1 in 100 ml of tetrahydrofuran were admixed with 3.32 g (42 mmol) of pyridine, 1.52 g of methoxyacetyl chloride and a catalytic amount of 4-dimethylaminopyridine. This mixture was heated at reflux with stirring for 16 h. The volatile components were removed under reduced pressure, the residue was taken up in 100 ml of ethyl acetate and the organic phase was washed successively three times with in each case 100 ml of 2 N HCl and once with saturated aqueous NaHCO$_3$ solution and dried over MgSO$_4$. The resulting diacetyl compound Va.69 (5.87 g) was directly reacted further: the reaction product was dissolved in 50 ml of methanol, 3.85 g (21.4 mmol) of a 30% by weight strength solution of sodium methoxide in methanol were added and the mixture was stirred at room temperature for 2 h. The mixture was then acidified with 1 N HCl and extracted three times with in each case 100 ml of methylene chloride, the combined organic phases were washed once with 100 ml of water and dried over MgSO$_4$ and the residue obtained after concentration was chromatographed on silica gel using cyclohexane/ethyl acetate (2/1 v/v). This gave 3.1 g of the anilide IIa.69.

$^1$H-NMR (CDCl$_3$) δ (ppm)=8.0 (br. s, 1H), 7.3 (d, 1H), 6.8 (t, 1H), 4.1 (s, 2H), 3.8 (s, 3H), 3.6 (s, 3H).

6.2 2-Methoxymethyl-4-chloro-6-fluoro-7-(4-chloro-5-difluoromethoxy-1-methyl-1H-pyrazol-3-yl)benzoxazole (6)

Reaction of 3.0 g (6.3 mmol) of anilide IIa.69 by the procedure described in 2.3 gave 0.98 g of the benzoxazole (6).

$^1$H-NMR (CDCl$_3$) δ (ppm) 7.3 (d, 1H), 6.8 (t, 1H), 4.8 (s, 2H), 3.9 (s, 3H), 3.5 (s, 3H).

EXAMPLE 7
Preparation of 2-cyclopropyl-4-chloro-6-fluoro-7-(4-chloro-5-trifluoromethyl-1-methyl-1H-pyrazol-3-yl)-benzoxazole (7)

7.1 2-Bromo-4-fluoro-6-chloro-3-(4-chloro-5-trifluoromethyl-1-methyl-1H-pyrazol-3-yl)aniline IVc.1

28 g (0.086 mol) of 4-fluoro-6-chloro-3-(4-chloro-5-trifluoromethyl-1-methyl-1H-pyrazol-3-yl)aniline (described in EP-A 0791571) were dissolved in 200 ml of acetic acid and admixed with 35 g (0.42 mol) of sodium acetate. 13.7 g (0.086 mol) of bromine were added dropwise to this mixture. The mixture was stirred overnight, the volatile components were removed under reduced pressure and the residue was taken up in 200 ml of dichloromethane.

This solution was washed with 2 N aqueous NaOH and dried over MgSO$_4$, and the residue obtained after concentration of the solution was chromatographed on silica gel using cyclohexane/ethyl acetate (4/1 v/v). This gave 20 g of the title compound IVc.1.

$^1$H-NMR (CDCl$_3$) δ (ppm) 7.2 (d, 1H), 4.5 (br. s, 2H), 4.0 (s, 3H).

7.2 N-Cyclopropylcarbonyl-2-bromo-4-fluoro-6-chloro-3-(4-chloro-5-trifluoromethyl-1-methyl-1H-pyrazol-3-yl)anilide IIc.85

2 g (4.9 mmol) of the aniline compound IVc.1 from 7.1 were dissolved in 10 ml of dichloromethane and 1 ml of pyridine. A spatula tip of 4-dimethylaminopyridine and 0.5 g (4.9 mmol) of cyclopropanecarbonyl chloride were added. The mixture was stirred for 16 h, diluted with 100 ml of water and extracted three times with in each case 50 ml of dichloromethane. The combined organic phases were dried over MgSO$_4$ and chromatographed on silica gel using cyclohexane/ethyl acetate (4/1 v/v).

1st Fraction: 1.2 g of diacyl compound Vc.85: $^1$H-NMR (CDCl$_3$) δ (ppm) 7.4 (d, 1H), 4.1 (s, 3H), 2.1 (m, 2H), 1.2 (m, 4H), 0.9 (m, 4H).

2nd Fraction: 0.8 g of monoacylanilide IIc.85: $^1$H-NMR (CDCl$_3$) δ (ppm) 7.3 (d, 1H), 7.1 (br. s, 1H), 4.1 (s, 3H), 1.6 (m, 1H), 1.2–0.8 (m, 4H).

The diacyl compound Vc.85 was dissolved in 20 ml of methanol, and the solution was admixed with 5 ml of 30% by weight strength sodium methoxide solution (in methanol) and stirred for 2 h. The solution was then admixed with 100 ml of methylene chloride and adjusted to pH 1 using 10% strength hydrochloric acid, and the organic phase was separated off. The residue obtained after drying and removal of the solvent was combined with fraction 1. This gave 2 g of the title compound IIc.85.

7.3 2-Cyclopropyl-4-chloro-6-fluoro-7-(4-chloro-5-trifluoro-methyl-1-methyl-1H-pyrazol-3-yl)benzoxazole (7)

2.0 g (4.2 mmol) of the anilide IIc.85 from step 7.2 in 20 ml of dimethylformamide and 2 ml of pyridine were admixed with 0.5 g (5 mmol) of KHCO$_3$. The mixture was stirred at 90° C. for 2 h, and 0.14 g (0.9 mmol) of Cu(I)Br was then added, and the mixture was heated with stirring at 140° C. for 4 h. The reaction mixture was concentrated and chromatographed on silica gel using cyclohexane/ethyl acetate. This gave 1.1 g of the benzoxazole (7).

$^1$H-NMR (CDCl$_3$) δ (ppm) 7.2 (d, 1H), 4.1 (s, 3H), 2.2 (m, 1H), 1.4–1.2 (m, 4H).

EXAMPLE 8

Preparation of 2-isopropyl-4-chloro-6-fluoro-7-(4-chloro-5-trifluoromethyl-1-methyl-1H-pyrazol-3-yl)benzoxazole (8)

8.1 N-Isopropylcarbonyl-2-bromo-4-fluoro-6-chloro-3-(4-chloro-5-trifluoromethyl-1-methyl-1H-pyrazol-3-yl)anilide IIc.17

The title compound IIc.17 was prepared from compound IVc.1 using the preparation procedure given in example 7.2.

$^1$H-NMR (CDCl$_3$) δ (ppm) 7.3 (d, 1H), 7.1 (br. s, 1H), 4.1 (s, 3H), 2.7 (septett, 1H), 1.3 (d, 6H).

8.2 2-Isopropyl-4-chloro-6-fluoro-7-(4-chloro-5-trifluoromethyl-1-methyl-1H-pyrazol-3-yl)benzoxazole (8)

Benzoxazole 8 was prepared from compound IIc.17 using the preparation procedure given in example 7.3.

$^1$H-NMR (CDCl$_3$) δ (ppm) 7.2 (d, 1H), 4.1 (s, 3H), 3.3 (septett, 1H), 1.3 (d, 6H).

EXAMPLE 9

Preparation of 2-methyl-4-chloro-6-fluoro-7-(4-chloro-5-trifluoromethyl-1-methyl-1H-pyrazol-3-yl)benzoxazole (9)

9.1 N-Acetyl-2-bromo-4-fluoro-6-chloro-3-(4-chloro-5-trifluoromethyl-1-methyl-1H-pyrazol-3-yl)anilide IIc.5

The title compound IIc.5 was prepared from compound IVc.1 using the preparation procedure given in example 7.2.

$^1$H-NMR (CDCl$_3$) δ (ppm) 7.3 (d, 1H), 7.1 (br. s, 1H), 4.1 (s, 3H), 2.2 (s, 3H).

9.2 2-Methyl-4-chloro-6-fluoro-7-(4-chloro-5-trifluoromethyl-1-methyl-1H-pyrazol-3-yl)benzoxazole (9)

Benzoxazole 9 was prepared from compound IIc.5 using the preparation procedure given in example 7.3.

$^1$H-NMR (CDCl$_3$) δ (ppm) 7.2 (d, 1H), 4.1 (s, 3H), 2.6 (s, 3H).

Preparation example for 2-bromo-4,6-dichloro-3-(4-bromo-5-difluoromethoxy-1-methyl-1H-pyrazol-3-yl)aniline The 2-bromo-4,6-dichloro-3-(4-bromo-5-difluoromethoxy-1-methyl-1H-pyrazol-3-yl)aniline IVa.4 used in example 1.2 was prepared alternatively to procedure 1.1 from 1,3-dichloro-4-(5-difluoromethoxy-1-methyl-1H-pyrazol-3-yl)benzene using the synthesis sequence described below:

10.1 2,4-Dichloro-5-(5-difluoromethoxy-1-methyl-1H-pyrazol-3-yl)nitrobenzene 3.0 g (10.2 mmol) of 1,3-dichloro-4-(5-difluoromethoxy-1-methyl-1H-pyrazol-3-yl)benzene were dissolved in 10 ml of concentrated sulfuric acid. At 0° C., 0.7 g (11.2 mmol) of 100% strength nitric acid was added dropwise, and the mixture was then stirred at 0° C.–10° C. for 1 h. The reaction mixture was then poured onto ice and the precipitate was filtered off with suction, washed with 100 ml of water and dried. This gave 3.24 g of the nitrobenzene as a yellow solid of melting point 134–137° C.

$^1$H-NMR (CDCl$_3$) δ (ppm) 8.4 (s, 1H), 7.6 (s, 1H), 6.6 (t, 1H), 6.4 (s, 1H), 3.8 (s, 3H).

10.2 2,4-Dichloro-5-(5-difluoromethoxy-1-methyl-1H-pyrazol-3-yl)aniline 1.5 g (4.2 mmol) of 2,4-dichloro-5-(5-difluoromethoxy-1-methyl-1H-pyrazol-3-yl)nitrobenzene were dissolved in a mixture of 50 ml of tetrahydrofuran and 50 ml of methanol and admixed with 4 g of Raney nickel. The mixture was stirred at room temperature under a gage pressure of 0.3 bar of hydrogen for 4 h and then filtered through kieselguhr. The filtrate was dried using magnesium sulfate and then evaporated to dryness. This gave 1.3 g of the aniline.

$^1$H-NMR (CDCl$_3$) δ (ppm) 7.4–7.1 (m, 2H), 6.6 (t, 1H), 6.4 (s, 1H), 4.1 (br. 2H), 3.8 (s, 3H).

10.3 2-Bromo-4,6-dichloro-3-(5-difluoromethoxy-1-methyl-1H-pyrazol-3-yl)aniline IVa.4

1 g (2.9 mmol) of 2,4-dichloro-5-(5-difluoromethoxy-1-methyl-1H-pyrazol-3-yl)aniline and 2.4 g (29 mmol) of sodium acetate were initially charged in 100 ml of glacial acetic acid, and 0.93 g (5.6 mmol) of bromine was added dropwise at room temperature. The reaction mixture was stirred overnight and then concentrated, and the residue was taken up in toluene and washed with 50 ml of 5% by weight strength aqueous sodium hydroxide solution until neutral. The organic phase was dried over magnesium sulfate and concentrated. This gave 1.3 g of the aniline IVa.4. The product that was obtained was identical to the compound obtained according to example 1.1.

USE EXAMPLES

The herbicidal activity of the compounds II, IV and V was demonstrated by greenhouse experiments:

The culture containers used were plastic pots containing loamy sand with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this was adversely affected by the active compounds.

For the post-emergence treatment, the test plants were first grown to a height of 3 to 15 cm, depending on the plant form, and only then treated with the active compounds which had been suspended or emulsified in water. For this purpose, the test plants were either sown directly and grown in the same containers, or they were first grown separately as seedlings and transplanted into the test containers a few days prior to treatment. The application rate for the post-emergence treatment was 31.3 g of a.s./ha.

Depending on the species, the plants were kept at 10–25° C. or 20–35° C. The test period extended over 2 to 4 weeks. During this time, the plants were tended, and their response to the individual treatments was evaluated.

The evaluation was carried out using a scale from 0 to 100. 100 means no emergence of the plants, or complete destruction of at least the above-ground parts, and 0 means no damage, or normal course of growth.

The plants used in the greenhouse experiments were composed of the following species:

| Bayer code | Common name |
| --- | --- |
| AMARE | velvet leaf |
| CHEAL | lamb's-quarters |
| BRAPL | marmalade grass |
| SETFA | giant foxtail |

Compounds that were examined:

IIa. 17: X = Br, Z = C(O)CH(CH$_3$)$_2$
IVa. 1: X = Br, Z = H
For comparison: X = Z = H At application rates of 31.3 g/ha, the compound No. IIa.17 shows very good herbicidal post-emergence activity against AMARE and CHEAL.

At application rates of 31.3 g/ha, the compound No. IVa.1 shows very good herbicidal post-emergence activity against AMARE, CHEAL, BRAPL and SETFA and, at application rates of 15.6 g/ha, shows very good activity against BRAPL and very good to good activity against SETFA. Both at application rates of 31.3 g/ha and at application rates of 15.6 g/ha, the comparative compound showed lower herbicidal activity against BRAPL and SETFA than the compound IVa.1.

Desiccant/defoliant Activity

The test plants used were young cotton plants with four leaves (without cotyledons) which had been grown under greenhouse conditions (relative atmospheric humidity 50–70%; day/night temperature 27/20° C.). The young cotton plants were subjected to foliar treatment to run-off point with an aqueous preparation of the active compound IIa.17 or IVa.1 (with addition of 0.15% by weight, based on the spray mixture, of a fatty alcohol ethoxylate (PLURAFAC LF 700 of BASF Aktiengesellschaft)). The amount of water applied was 1000 l/ha (converted). After 13 days, the number of leaves shed and the degree of defoliation in percent were determined. The untreated control plants did not shed any leaves.

We claim:

1. A process for preparing 7-(pyrazol-3-yl)benzoxazoles of the formula I (I)

in which the variables $R^1$–$R^6$ are as defined below:

$R^1$ is hydrogen, $C_1$–$C_4$-alkyl or $C_1$–$C_4$-haloalkyl;

$R^2$ is cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl;

$R^3$ is hydrogen, halogen, cyano, $C_1$–$C_4$-alkyl or $C_1$–$C_4$-haloalkyl;

$R^4$ is halogen;

$R^5$ is fluorine, chlorine or cyano;

$R^6$ is hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_1$–$C_4$-alkoxy-$C_1$–$C_4$-alkyl, $C_1$–$C_4$-cyanoalkyl, $C_1$–$C_4$-alkylthio-$C_1$–$C_4$-alkyl, ($C_1$–$C_4$-alkoxy)carbonyl-$C_1$–$C_4$-alkyl, $C_3$–$C_8$-cycloalkyl, $C_3$–$C_8$-cycloalkyl-$C_1$–$C_4$-alkyl, $C_3$–$C_8$-cycloalkyloxy-$C_1$–$C_4$-alkyl, phenyl, phenyl-$C_1$–$C_4$-alkyl, or where each cycloalkyl, phenyl and heterocyclyl ring can be unsubstituted or may carry one, two or three substituents selected independently of one another from the group consisting of cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio;

which comprises reacting a 2-halo-3-(pyrazol-3-yl)anilide of the formula II

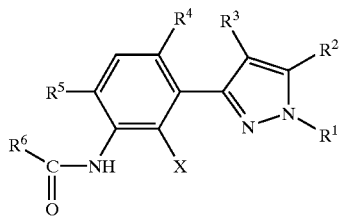

(II)

in which the variables R¹–R⁶ are as defined above and X is bromine or iodine in the presence of a copper(I) compound and a base to give a compound of the formula I, wherein the molar ratio of copper(I) compound to the compound II used is <1:1.

2. A process as claimed in claim 1, wherein the molar ratio of transition metal to the compound II used is in the range from 0.05:1 to 0.5:1.

3. A process as claimed in claim 1, wherein the base is selected form the alkoxides, amides, hydries, hydroxides, bicarbonates and carbonates of alkali metals and of alkaline earth metals.

4. A process as claimed in claim 1, wherein an at least equimolar amount of base, based on the compound of the formula II, is employed.

5. A process as claimed in claim 1, wherein the conversion of the compound of the formula II into compound of the formula I is carried out in a polar aprotic solvent or solvent mixture, where the solvent is selected from the group consisting of dimethylformamide (DMF), dimethyl sulfoxide (DMSO), N-methylpyrrolidone (NMP), N,N-dimethylacetamide (DMA), acetonitrile, propionitrile, pyridine and dimethyldi- or triethylene glycols and mixtures thereof.

6. A process as claimed in any of the preceding claims, wherein the variables R¹–R⁶ of an at least equimolar amount of base, based on the compound of the formula II, is employed.

7. A process as claimed in any of the preceding claims, wherein the conversion of compound II into compound I is carried out in a polar aprotic solvent or solvent mixture, where the solvent is selected from the group consisting of dimethylformamide (DMF), dimethyl sulfoxide (DMSO), N-methylpyrrolidone (NMP), N,N-dimethylacetamide (DMA), acetonitrile, propionitrile, pyridine and dimethyldi- or triethylene glycols and mixtures thereof.

8. A process as claimed in claim 1, wherein a compound II is reacted in which the variables R¹–R⁶ are as defined below:

R¹ is hydrogen, methyl or ethyl;
R² is cyano, difluoromethoxy, trifluoromethoxy or methylsulfonyl;
R³ is halogen;
R⁴ is halogen;
R⁵ is fluorine, chlorine or cyano;
R⁶ is hydrogen, $C_1$–$C_4$-alkyl, $C_1$–$C_4$-haloalkyl, $C_2$–$C_4$-alkenyl, $C_2$–$C_4$-haloalkenyl, $C_2$–$C_4$-alkynyl, $C_1$–$C_4$-alkoxy-$C_1$–$C_4$-alkyl, $C_1$–$C_4$-alkoxycarbonyl-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl, 4- to 7-membered heterocyclyl or heterocyclyl-$C_1$–$C_4$-alkyl, where the phenyl ring, the cycloalkyl ring and the heterocyclyl ring can be unsubstituted or may carry one or two substituents, selected from the group consisting of cyano, halogen, $C_1$–$C_4$-alkyl, $C_1$–$C_4$-haloalkyl and $C_1$–$C_4$-alkoxy.

9. A process as claimed in claim 8, which additionally comprises the following process teps for preparing the compounds of the formula III-A;

a. nitration of a 3-(pyrazol-3-yl)benzene of the formula VI-A,

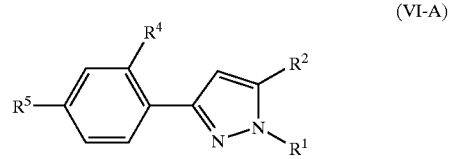

(VI-A)

in which R¹, R², R⁴ and R⁵ are as defined above to give a 3-(pyrazol-3-yl)-1-nitrobenzene of the formula VII-A and

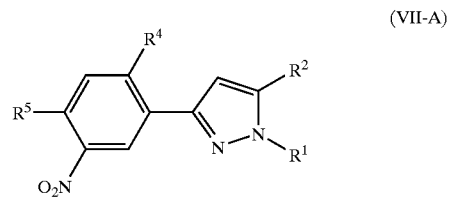

(VII-A)

B. reaction of VII-A with a reducing agent to give a 3-(pyrazol-3-yl)aniline of the formula III-A

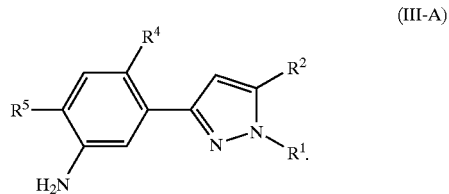

(III-A)

* * * * *